(12) United States Patent
Smith

(10) Patent No.: US 6,509,313 B1
(45) Date of Patent: *Jan. 21, 2003

(54) STIMULATION OF IMMUNE RESPONSE WITH LOW DOSES OF CYTOKINES

(75) Inventor: Kendall A. Smith, New York, NY (US)

(73) Assignee: Cornell Research Foundation, Inc., Ithica, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/646,098

(22) Filed: May 7, 1996

Related U.S. Application Data

(63) Continuation-in-part of application No. 08/608,516, filed on Feb. 28, 1996, now Pat. No. 6,045,788.

(51) Int. Cl.$^7$ ............................................. A61K 38/00
(52) U.S. Cl. ................................ 514/2; 514/8; 514/12; 514/885; 424/85.1; 424/85.2; 424/184.1; 424/198.1
(58) Field of Search .......................... 514/2, 8, 12, 885; 424/85.1, 85.2, 184.1, 198.1

(56) References Cited

U.S. PATENT DOCUMENTS

| | | | | |
|---|---|---|---|---|
| 4,933,433 | A | 6/1990 | Tamblyn ..................... | 530/351 |
| 4,938,956 | A | 7/1990 | Howard et al. ............. | 424/85.2 |
| 4,940,456 | A | 7/1990 | Sibalis et al. ................. | 604/20 |
| 5,004,605 | A | 4/1991 | Hershenson et al. ........ | 424/85.6 |
| 5,026,687 | A | 6/1991 | Yarchoan et al. ............. | 514/45 |
| 5,126,129 | A | 6/1992 | Wiltrout et al. ............ | 424/85.2 |
| 5,145,677 | A | 9/1992 | von Eichborn et al. ..... | 424/85.5 |
| 5,208,018 | A | 5/1993 | Gough ....................... | 414/85.7 |
| 5,229,109 | A | 7/1993 | Grimm et al. ............. | 424/85.2 |
| 5,236,707 | A | 8/1993 | Stewart, II ................. | 424/85.7 |
| 5,376,368 | A | 12/1994 | Ulich ........................ | 424/85.2 |
| 5,420,109 | A | 5/1995 | Suto et al. ...................... | 514/8 |
| 5,474,769 | A | 12/1995 | Grabstein et al. .......... | 424/85.2 |
| 6,045,788 | A | * 4/2000 | Smith ........................ | 424/85.2 |

FOREIGN PATENT DOCUMENTS

| | | |
|---|---|---|
| EP | 0 118 977 | 9/1984 |
| EP | 0 254 593 | 1/1988 |
| EP | 0 353 910 | 2/1990 |
| EP | 0 378 171 | 7/1990 |
| EP | 0 405 315 | 1/1991 |
| EP | 0 533 416 | 3/1993 |
| EP | 0 640 336 | 3/1995 |
| WO | WO88/03411 | 5/1988 |
| WO | WO90/14432 | 11/1990 |
| WO | WO91/01143 | 2/1991 |
| WO | WO92/05256 | 4/1992 |
| WO | WO92/08792 | 5/1992 |
| WO | WO92/13568 | 8/1992 |
| WO | WO95/27722 | 10/1995 |
| WO | WO96/04013 | 2/1996 |
| WO | WO96/30515 | 10/1996 |
| WO | WO96/36350 | 11/1996 |

OTHER PUBLICATIONS

Yang et al. (1995) Cancer, vol. 76, No. 4, pp. 687–694.*
Smith, K.A., "Cell Growth signal Transduction Is Quantal", Receptor Activation by Antigens, Cytokines, Hormones, and Growth Factors, vol. 766, Ann. N.Y. Acad. Sci. (1995).
Ihle, J.N., "STATs: Signal Transducers and Activators of Transcription", Cell 84:331 (1996).
Moriggl, R. et al., "Stat5 Is Required for IL–2–Induced Cell Cycle Progression of Peripheral T Cells", Immunity 10: 249–259 (Feb. 1999).
Watowich, S.S. et al., "Cytokine Receptor Signal Transduction and the Control of Hematopoietic Cell Development", Annu. Rev. Cell Dev. Biol., 12: 91–128 (1996).
Morikawa, K. et al, Enhancement of Therapeutic Effects of Recombinant Interleukin 2 on a Transplantable Rat Fibrosarcoma by the Use of a Sustained Release Vehicle Pluronic Gel, Cancer Research, 47:37–41, 1987.
Michael A. Caliguiri et al., "Extended Continuous Infusion Low–Dose Recombinant Interleukin–2 in Advanced Cancer: Prolonged Immunomodulation Without Significant Toxicity", Journal of Clinical Oncology, vol. 9, No. 12, (12/91), pp. 2110–2119.
Zale P. Bernstein et al., "Prolonged Administration of Low––Dose Interleukine–2 in Human Immunodeficiency Virus–Associated Malignancy Results in Selective Expansion of Innate Immune Effectors Without Significant Clinical Toxicity," Blood, vol. 86, No. 9, (1995) pp. 3287–3294.
Hedy Teppler et al., "Efficacy of Low Doses of the Polyethylene Glycol Derivative of Interleukine–2 in Modulating the Immune Response of Patients with Human Immunodeficiency Virus Type 1 Infection," The Journal of Infectious Diseases, (1993), 167, pp. 291–298.

* cited by examiner

Primary Examiner—Dwayne C. Jones
Assistant Examiner—C. Delacroix-Muirheid
(74) Attorney, Agent, or Firm—Darby & Darby

(57) ABSTRACT

A method of activating the immune system of a subject comprises the chronic administration of low doses of an agent having cytokine activity, including natural and recombinant cytokines, fragments, analogues, fusion proteins, and derivatives thereof, that are pharmaceutically acceptable, and their mixtures with other biologically active agents and formulation ingredients. The agent is provided as a unit dosage form, in systemic and topical product form, as an implant, inhalant, transdermal delivery device, and ultrasound and electrotransport devices, as well as in the form of a kit for self-administration.

57 Claims, 2 Drawing Sheets

| | Grade 0 | Grade 1 | Grade 2 | Grade 3 | Grade 4 |
|---|---|---|---|---|---|
| Hemtologic (Adults) Hemoglobin (g/100ml) Leukocytes 1000/cmm Granulocytes 1000/cmm Platelets 1000/cm | >11.0 | 9.5-10.9 | 8.0-9.4 | 6.5-7.9 | <6.5 |
| Hemorrhage | none | petechiae | mild blood loss | gross blood loss | debilitating blood loss |
| Gastrointestinal Bilirubin | <1.25 x N* | 1.26-2.5xN | 2.6-5xN | 5.1-10xN | >10xN |
| SGOT/SGPT | <1.25 x N* | 1.26-2.5xN | 2.6-5xN | 5.1-10xN | >10xN |
| Alkaline Phosphatase | <1.25 x N* | 1.26-2.5xN | 2.6-5xN | 5.1-10xN | >10xN |
| Oral | none | soreness/ erythema | erythema, ulcers, cannot eat solids transient vomiting | | aliment-ation possible intractable vomiting |
| Nausea/Vomiting | none | nausea | | | |
| Diarrhea | none | transient <2 days | tolerable but >2 days | intolerable requiring therapy | hemorragic dehyd. |
| Renal, Bladder, BUN or Blood Urea | <1.25 x N* | 1.26-2.5xN | 2.6-5xN | 5.1-10xN | >10xN |
| Creatinie | <1.25 x N* | 1.26-2.5xN | 2.6-5xN | 5.1-10xN | >10xN |
| Proteinuria | none | 1+ <0.3g/100ml | 2-3+ 0.3-1.0g/100 ml | 4+ >1.0g/100ml | nephritic syndrome |
| Hematuria | none | microscopic | gross | gross+clots | ob-structive uropathy |
| Fever Drug | none | fever <38C | fever 38C-40C | fever >40C | fever with hypo tension |
| Allergic | none | edema | bronchospasm no parenteral therapy needed | brochospasm parenteral therapy req'd | anaphy-laxis |

Figure 1A

|  | Grade 0 | Grade 1 | Grade 2 | Grade 3 | Grade 4 |
|---|---|---|---|---|---|
| Cutaneous | none | erythema | dry desquamation, vesiculation pruritus | moist desquamation, ulceration | exfoliative dermatitis necrosis requiring surgical intervention |
| Hair | none | minimal hair loss | moderate, patchy alopecia but alopecia reversible | complete alopeciaible | non-revers |
| Infection (specify site) | none | minor infection | moderate infection | major infection | major infection with hypotension |
| Cardiac Rhythm | none | sinus tachycardia > 110 at rest | unifocal PVC atrial arrythmia | multifocal PVC | ventricular tachycardia |
| Function | none | asymptomatic, but abnormal cardiac sign | transient symptomatic dysfunction, no therapy req'd | symptomatic dysfunction, responsive to therapy | symptomatic dysfunction, non-responsive to therapy |
| Pericarditis | none | asymptomatic effusion | symptomatic, no tap req'd | tamponade, tap req'd | tamponade, surgery req'd |

Figure 1B

STIMULATION OF IMMUNE RESPONSE WITH LOW DOSES OF CYTOKINES

This is a continuation-in-part application of U.S. Ser. No. 08/608,516, entitled "Stimulation and/or Maintenance of Immune Response with Low Doses of IL-2 & Related Agents, Various Compositions & Other Products", filed Feb. 28, 1996, by the present inventor, now U.S. Pat. No. 6,045,788.

The present invention was made at least partially with Government funds under Grants Nos. RO1-AI32031-20 and MO1-RR0047. The US Government may have rights in this patent.

BACKGROUND OF THE INVENTION

1. Field of the Invention

This invention relates to the field of immunotherapy, and more particularly immunotherapy with low doses of cytokines.

The present method and products are suitable for the treatment of diseases or conditions such as microbial infections, cancer and the like.

2. Description of the Background

In the immune system, there are three major types of lymphocytes: B cells, T cells, and natural killer (NK) cells. B-cells are derived from bone marrow, and comprise about 10% of the lymphocytes found circulating in blood. When stimulated by a specific antigen, each B-cell differentiates into a plasma cell that secretes antibodies of a single specificity. T-cells mature in the thymus and, make up about 80% of circulating lymphocytes. Although not producing antibodies, T-cells bear on their surfaces specific antigen receptors resembling antibody molecules. T-cells react to antigen stimulation by secreting immunomediator molecules or cytokines (helper T-cells), and toxic molecules (cytotoxic T-cells). Cytotoxic T-cells act directly on infected cells, and by secreting toxic molecules kill them and any foreign particles, such as microorganisms, they may contain. NK cells, make up about 10% of the lymphocyte population, and are not antigen specific, but recognize and kill cells infected with microbes. Monocytes and macrophages are large scavenger cells that ingest foreign particles and present antigens to the T-cells, which trigger specific immune responses. When an antigen is introduced, it is initially ingested by macrophages and other antigen presenting cells. After digestion, short segments thereof are presented on their cell surfaces. Only a few of all circulating T-cells have receptors that specifically bind to the antigen, and this binding stimulates the T-cells to secrete cytokines.

Cytokines are small proteins secreted primarily, but not exclusively, by cells of the immune system that promote the proliferation and/or differentiative functions of other cells. Examples of cytokines include interleukins, interferons, hematopoietic colony stimulating factors (CSF), and proinflammatory factors such as tumor necrosis factor (TNF). The therapeutic stimulation of the immune system has yet to find broad applications because of the difficulty in avoiding toxicity, which is part and parcel of immune-mediated inflammation. The toxicity associated with immunoreactivity is familiar to everyone as the signs and symptoms that occur during microbial infections, such as fever, fatigue, malaise and myalgia. These toxic symptoms were originally thought to be caused by substances, such as toxins, released or produced by the microbes themselves. Within the past decade, however, it has gradually become appreciated that the toxic signs and symptoms associated with microbial infection are attributable to molecules termed cytokines released, upon activation, by the immune system. When stimulated, for example, by microbes, the immune system produces the cytokines, which themselves, i.e. not the microbial toxins, produce the recognizable unpleasant and harmful effects. This was proven when the cytokines themselves were isolated, purified and injected into experiential animals and humans.

Despite producing toxic symptoms, the cytokines are primarily responsible for regulating the immune system. They determine the onset, magnitude, and duration of the immune response by stimulating the proliferation and differentiation of various types of cells comprising the immune system, including all of the white blood cells (leukocytes) that are recognizable as lymphocytes, monocytes/macrophages, polymorphonuclear leukocytes (PMN), and specialized antigen-presenting cells (APCs). When it was realized that cytokines regulate the immune system, it was hoped that they could be used therapeutically, to boost or augment immune reactivity in the treatment of microbial infections, malignancies, and for various immunodeficient states, such as the Acquired Immune Deficiency Syndrome (AIDS). However, the high and sometimes intolerable toxicities associated with cytokine administration have precluded their widespread use, especially in asymptomatic individuals afflicted with an infection or illness without signs or symptoms, such as infection with the Human Immunodeficiency Virus (HIV).

The toxicities associated with the administration of various cytokines at high doses are severe. For example, one of the first cytokines to be discovered, interleukin 2 (IL-2), was used initially to treat cancer in very high doses, up to $150 \times 10^6$ IU/day (10 mg/day). This resulted in extremely toxic side effects, including capillary leak with hypotension and high fever (>39° C.). This limited the duration of IL-2 therapy to only a few days, and restricted its use to solely patients hospitalized in the intensive care unit.

Over the past several years, lower doses of cytokines have been administered in attempts to circumvent most of the toxicities, while hoping to still retain at least some of the immune enhancing effects. For example, Caliguri and co-workers, including the inventor, found that ambulatory cancer patients could tolerate IL-2 administered as a continuous intravenous (IV) infusion for up to 90 days with minimal toxicities (WHO Grade 1, see table) provided the dose was in the range of $2.5-5.0 \times 10^5$ IU/m$^2$ body surface area per day. Most importantly, even though the dose was lowered about 600-fold from the original dose used earlier in the treatment of cancer, there were still detectable augmenting effects on the immune system, notably a gradual increase in the concentration of circulating Natural Killer (NK) cells. Similar results were recently reported by Bernstein and co-workers, who administered IL-2 subcutaneously (s.q.) to patients suffering from AIDS-associated malignancies, in doses ranging from $0.5-1.0 \times 10^6$ IU for 3 months. In a separate study, Teppler and co-workers, including the present inventor, injected IL-2 daily for 30 days intradermally (i.d.) into asymptomatic HIV+ individuals. At a dose of $0.18 \times 10^6$ IU/day given for this short interval, no untoward toxic effects were noted, but neither was there an increase in circulating leukocytes.

Thus far, the following four (4) families of cytokines that regulate the immune system, are recognizable according to their structures.

1) The interleukin family includes cytokines such as IL-2, 3, 4, 5, 6, 7, 9, 12, 13, and 15. These cytokines are small (10–20 kDaltons) proteins that all share a 3 dimensional structure of 4 antiparallel alpha helices. The receptors of this cytokine family share amino acid sequence homologies, especially in their extracellular domains.

2) The tumor necrosis factor (TNF) family includes compounds such as TNF-α, TNF-β (lymphotoxin), nerve growth factor (NGF), and the CD40, Fas, CD27, and CD30 ligands. The ligands of this family are either secreted or remain membrane anchored, and function as homotrimers of about 15 kDalton monomers. The receptors of this family share amino acid sequence homologies.

3) The interferon (IFN) family includes compounds such as IFN-α, IFN-β, and IFN-γ, and is distinguished by the unique biologic property of stimulating cells to prevent viral replication.

4) The chemokine family includes molecules such as IL-8, macrophage inhibiting protein (MIP), and Rantes. These cytokines are small (about 10 kDaltons), and bind to a distinct family of receptors that have 7 membrane spanning alpha helices, and that are coupled to guanine nucleotide binding proteins (G proteins).

Even though these distinct cytokine families may be classified based upon their structure, they have in common the properties of being produced in, and/or being active on, the mammalian immune system.

Interleukin 2 (IL-2), for example, was one of the first cytokines to be identified and characterized. It is produced exclusively by T-lymphocytes in response to stimulation by antigens. IL-2 acts on the three major types of lymphocytes, including T cells, B cells, and NK cells, stimulating them to proliferate and augmenting their differentiative functions. IL-2 potentiates both innate or natural host defenses by stimulating NK cells, and antigen-specific acquired immune reactivity by stimulating T cells and B cells.

In vitro studies have shown that IL-2 mediates its effects by binding to specific receptors (IL-2R) expressed on the surfaces of IL-2-responsive target cells. When IL-2 binds to its receptors, it initiates a series of intracellular events that result in the activation of a set of genes, the products of which determine the cellular responses observed, such as cellular proliferation. Thus, one of the consequences of IL-2 stimulation is an expansion in the number of T-cells, B-cells and NK cells. IL-2 also stimulates the expression of genes encoding other cytokines, especially by T-cells and NK cells. In particular, IL-2 stimulation of NK cells results in their production of secondary, pro-inflammatory cytokines, including TNFα, IFN-γ and GM-CSF. These NK cell-derived cytokines, in turn, are potent stimuli for monocytes, promoting their production of further pro-inflammatory cytokines. Thus, although IL-2 is attractive as an immunotherapeutic agent, given that it stimulates all of the major types of lymphocytes, its therapeutic use has been impeded by its toxicity, most of which has been attributed to the release of large quantities of secondary cytokines. Clearly, the major problem associated with the administration of IL-2 has been its toxicity, which has prevented its use in therapy for a wide range of illnesses and indications.

Various studies on IL-2 immunotherapy have been reported, the initial ones dating back to 1984. Since that time, various doses, routes of administration and schedules of administration have been tried. However, up to the present time, IL-2 has only been approved by the Food and Drug Administration for limited use in patients with renal cell carcinoma. For this purpose, the high doses of IL-2 used, only permit its administration for 1–2 weeks before severe toxicity develops. Additional rounds of treatment administered after discontinuance proved ineffective.

Throughout this patent, where possible, all reported cytokine units of biological activity have been converted to International Units (IU) to enable a comparison of the doses of the same cytokine used in different studies. Also, where possible, and when appropriate, cytokines will be referred to as the amount of protein, in weight or moles for uniformity's sake. In addition, some agents' doses are expressed as either IU or moles per $m^2$ of body surface area (BSA). The BSA values are easily calculated from similar values based on a subject's weight and height using a standard conversion table of height and weight measurements. For example, a 70 kg. person of normal height has 1.5 $m^2$ BSA. Doses of 0.15 to $15 \times 10^6$ IU impure, natural IL-2/$m^2$/day were administered to severely ill AIDS patients by subcutaneous (s.q.) or intravenous (i.v.) injection for a short period (3 weeks) or for 5 days/week for 4 weeks. Neither significant toxicity nor improvements in immunologic parameters were seen. The first administration of recombinant interleukin-2 (rIL-2) was reported in 1985, when cancer patients were given intermittent daily doses of up to $70 \times 10^6$ IU rIL-2/$m^2$/day for 1–2 weeks, with severe toxicity WHO grades 3 and 4. (See, Table 3 below). In spite of the severe toxicity elicited, this dose continued to be used, with minor variations on dose and schedule, in the past 10 years in the treatment of many malignancies and other indications because of its beneficial anti-tumor effect. The doses used varied from $5 \times 10^3$ and $12 \times 10^6$ IU IL-2/$m^2$/day and the time of administration varied from just a few days to 90 days, in some cases the administration being done only a few days every week. These studies proved disappointing, mostly due to their lack of efficacy or to the toxicity elicited, which varied from grade 1 to grades 3 and 4 in some cases, or both. U.S. Pat. No. 5,026,687 discloses the use of ddI for the treatment of HIV+ patients. Example 8 is a paper example forecasting the oral administration of ddI in combination with an all encompassing dose of IL-2 (25,000–1,000,000 U/day) by continuous infusion or other systemic administration for a period of 3 months. Although the example indicates that "beneficial results are seen", because of its hypothetical nature, it provides no real information on IL-2 toxicity since no enabling work was provided. In summary, immunotherapy with high doses (greater than $1 \times 10^6$ IU/$m^2$/day) of IL-2 has been shown to lead to severe, unacceptable toxicity WHO grades 2 and higher, requiring hospitalization. These doses are only tolerable for a few days, and result in only transient detectable improvements in immune function. Lower doses ($0.1–0.5 \times 10^6$ IU rIL-2/$m^2$/day) have been administered for up to 90 days but resulted in toxicity WHO grade 1, with only transient increases in immunological function.

Thus, up until the time of this invention, the view was widely held that the use of cytokines was ineffective in some diseases, and contraindicated, for example, in patients with HIV infection due to its potential for activating or increasing replication of HIV. More generally, up to the present time, no long term cytokine therapy has been proven suitable, effective and safe, for the treatment of HIV infected individuals in the absence of severe side effects. Nor have there been any reports on the administration of cytokines to immune impaired infants or mammalian animals, or to normal individuals, infants or mammalian animals which may be temporarily afflicted with an infection or other condition, and who would benefit from a temporary stimulation of their immune system to overcome the condition.

Accordingly, up to the present invention, it was not believed possible to administer cytokines, whether in a preventative or therapeutic mode, for prolonged periods of time, so that individuals could carry on normal lives and experience improved immune function, without eliciting toxicity. Moreover, up to the present time, cytokines had never been administered to asymptomatic individuals for longer than 30 days, so that the long-term effects of its chronic administration remained unknown.

Thus, there is still a need for a maintenance method of administering agents having cytokine activity at a dose which stimulates the immune system, while producing minimal or no toxicity and/or detrimental side effects which have precluded the continued administration of the same cytokines, alone and/or in combination with other therapeutic agents. Such method would permit the effective avoidance, and/or amelioration of symptoms, which afflict certain subjects with decreased immune response or an impaired immune system, in a safe manner, permitting them to resume an active life schedule.

SUMMARY OF THE INVENTION

This invention relates to a unit dosage composition comprising, in a sterile container, an agent having cytokine activity, including natural, recombinant and mutated cytokines, fragments, analogs, and derivatives of the cytokines, and mixtures thereof. The composition is also provided as a kit with single or multiple unit dosages of the composition, instructions, and device(s) for its administration, such as needles and syringes, inhalators, and the like. The composition may be provided in various forms, including topical and systemic forms, such as powders, creams, ointments, sprays, solutions, suppositories, powders, suspensions, patches, emulsions, implants, and encapsulated particles, among others, and may contain other therapeutic agents, such as various forms of the cytokines, including natural, recombinant and mutated forms, fragments, fusion proteins, and other analogues and derivatives of the cytokines, mixtures, other biologically active agents and formulation additives, and mixtures thereof. Topical and controlled release formulations, implants, inhalators, and transdermal, intradermal, transbuccal, and transpulmonary delivery devices, among others, are also included.

The composition of the invention may be self-administered by any topical or systemic route, as long as its peptide bonds are protected from degradation. The present agent is suitable for the chronic stimulation and/or maintenance and/or inhibition of immune response in a subject when administered at a dose effective to activate high affinity cytokine receptors without eliciting substantial toxicity, i.e., WHO group 1 or higher. The amount of the agent administered may be determined as described herein, and is preferably effective to produce about 10 to about 90% or higher saturation of the biologically relevant, high affinity cytokine receptors. The present immunotherapy is useful for stimulating and/or inhibiting the immune system in the prevention and treatment of malignancies, of mild and severe infections afflicting normal individuals, of opportunistic infections generally arising in immunocompromised individuals, such as viral, fungal, parasitic, and bacterial infections, including patients infected with the human immunodeficiency virus (HIV), and infections frequently encountered after operations or procedures, such as bone marrow transplants (BMT), inflammation, necrosis, sepsis, and as an adjuvant for vaccines, among other applications. The present immunotherapy is also generally suitable for the stimulation or inhibition of the immune system in general or of specific immune responses, in normal subjects, children, and the elderly, and for use in animals in general.

BRIEF DESCRIPTION OF THE FIGURE

FIG. 1A and FIG. 1B show a table of the recommendations for WHO grading of acute and sub-acute toxicity. This Table lists the specific toxicity symptoms and their classification by severity in Grades 0 to 4.

DESCRIPTION OF THE PREFERRED EMBODIMENTS

The present invention arose from a desire by the inventor to improve on prior art technology. In the past, short term cytokine therapy had been attempted with, for example, IL-2 on HIV+ patients, on patients suffering from some forms of cancer, and even on patients that had been subjected to bone marrow transplant (BMT). Other cytokines have also been utilized therapeutically in high doses for short periods of time. However, high doses of many cytokines, including IL-2, were shown to bring about extremely severe side effects, such as those classified by the World Health Organization (WHO) as Grades 1 to Grade 4 toxicities. Trials have been designed to reduce the toxic effects of, for example IL-2, by administering to the patient antibodies blocking the subsequent cascade effects produced by high doses of IL-2. (e.g., combined IL-2/anti-TNF antibodies).

This invention, thus, relates to the use of cytokines as immunotherapeutic agents in amounts that do not produce toxic side effects that are detrimental to the well being and/or life stile of the patient, and permit their administration for prolonged periods of time without the need arising for discontinuing therapy or masking or countering the undesirable effects of the drug. The present therapy may be applied to symptomatic and asymptomatic individuals for prolonged periods of time, in excess of 12 months, and even several years, without producing toxic side effects. The safe, non-toxic use of cytokines relies on information of the cytokines' binding to its high affinity receptor. As all known cytokines promote their effects by binding to high affinity, specific receptors, the principles demonstrated below for IL-2, are applicable to all other cytokines. In many cases, high doses of the cytokines, such as IL-2, were shown to bring about extremely severe side effects, such as those classified by the World Health Organization (WHO) as grades 1 to 4 toxicities. Such is the case of the interferons (IFNs), IL-12, and the pro-inflammatory cytokines (IL-6, TNF-α, TNF-α), which have been shown to cause similar signs and symptoms (WHO grades 1 to 4), as does IL-2. The specific symptoms and their classification by severity as classified by the WHO are shown in Table 2 below.

TABLE 2

Recommendations for WHO Grading of Acute and Sub-acute Toxicity

| | Grade 0 | Grade 1 | Grade 2 | Grade 3 | Grade 4 |
|---|---|---|---|---|---|
| Hematologic (Adults) | | | | | |
| Hemoglobin (g/100 ml) | >11.0 | 9.5–10.9 | 8.0–9.4 | 6.5–7.9 | <6.5 |
| Leukocytes 1000/cmm | >4.0 | 3.0–3.9 | 2.0–2.9 | 1.0–1.9 | <1.0 |
| Granulocytes 1000/cmm | >2.0 | 1.5–1.9 | 1.0–1.4 | 0.5–0.9 | <0.5 |
| Platelets 1000/cmm | >100 | 75–99 | 50–74 | 25–49 | <25 |
| Hemorrhage | none | petechiae | mild blood loss | gross blood loss | debilitating blood loss |
| Gastrointestinal | | | | | |
| Bilirubin | <1.25 × N* | 1.26–2.5 × N | 2.6–5 × N | 5.1–10 × N | >10 × N |
| SGOT/SGPT | <1.25 × N* | 1.26–2.5 × N | 2.6–5 × N | 5.1–10 × N | >10 × N |
| Alkaline phosphatase | <1.25 × N* | 1.26–2.5 × N | 2.6–5 × N | 5.1–10 × N | >10 × N |
| Oral | none | soreness/erythema | erythema, ulcers, can eat solids | ulcers, requires liquid diet only | alimentation not possible |
| Nausea/vomiting | none | nausea | transient vomiting | vomiting requiring therapy | intractable vomiting |
| Diarrhea | none | transient <2 days | tolerable but >2 days | intolerable requiring therapy | hemorrhagic dehyd. |
| Renal, bladder | | | | | |
| BUN or blood urea | <1.25 × N | 1.26–2.5 × N | 2.6–5 × N | 5–10 × N | >10 × N |
| Creatinie | <1.25 × N | 1.26–2.5 × N | 2.6–5 × N | 5–10 × N | >10 × N |
| Proteinuria | none | 1 + <0.3 g/100 ml | 2–3 + 0.3–1.0 g/100 ml | 4 + >1.0g/100 ml | nephrotic syndrome |
| Hematuria | none | microscopic | gross | gross + clots | obstructive uropathy |
| Pulmonary | none | mild symptoms | exertional dyspnea | dyspnea at rest | complete bed rest req'd |
| Fever–Drug | none | fever <38 C. | fever 38 C.–40 C. | fever >40 C. | fever with hypotension |
| Allergic | none | edema | bronchospasm no parenteral therapy needed | bronchospasm parenteral therapy req'd | anaphylaxis |
| Cutaneous | none | erythema | dry desquamation, vesiculation pruritus | moist desquamation, ulceration | exfoliative dermatitis necrosis requiring surgical intervention |
| Hair | none | minimal hair loss | moderate, patchy alopecia | complete alopecia but reversible | non-reversible alopecia |
| Infection (specify site) | none | minor infection | moderate infection | major infection | major infection with hypotension |
| Cardiac | | | | | |
| Rhythm | none | sinus tachycardia >110 at rest | unifocal PVC atrial arrythmia | multifocal PVC | ventricular tachycardia |
| Function | none | asymptomatic, but abnormal cardiac sign | transient symptomatic dysfunction, no therapy req'd | symptomatic dysfunction, responsive to therapy | symptomatic dysfunction, non-responsive to therapy |
| Pericarditis | none | asymptomatic effusion | symptomatic, no tap req'd | tamponade, tap req'd | tamponade, surgery req'd |

The present inventor has now unexpectedly found that low doses of agents having cytokine activity, such as natural and recombinant cytokines, including IL-2, 3, 4, 5, 6, 7, 9, 10, 11, 12, 13, 14, and 15, the tumor necrosis factor (TNF)

family including TNF-α, IFN-β (lymphotoxin), nerve growth factor (NGF), CD40, Fas, CD27, CD30, the interferon (IFN) family including IFN-α, IFN-β, and IFN-γ, the chemokine family including IL-8, macrophage inhibiting protein (MIP), and Rantes, and others, active fragments, pharmaceutically acceptable analogues and derivatives thereof, and mixtures thereof, may be continuously administered to patients for prolonged periods of time to activate, stimulate, and/or inhibit their immune system in the substantial absence of toxicity WHO grade 1, 2, 3, or higher. This technology is beneficially applied to patients afflicted with a microbial infection, including viral (e.g. HIV+), bacterial, fungal, and other types of infection, inflammation, necrosis, sepsis, to cancer patients, and even to patients that had been subjected to bone marrow transplant (BMT), and as a vaccine adjuvent. In addition, this therapy may be applied to normal individuals, children and the elderly when a boost of their immune system is desired or required. In the remainder of this patent, the narrative will generically refer to IL-2, IL-12, IL-15, IFN-α, IFN-γ, IFN-β, the CD-40 ligand, and more generally to cytokines, but the present teachings, unless otherwise indicated, extend to all of the agents encompassed herein.

Thus, the present treatment achieves therapeutic benefits without producing toxic effects. In vitro experiments have shown that cytokines promote their effects by binding to specific, high affinity receptors expressed on the cell surface. When cytokines bind to their receptors, they often promote the production of additional cytokines, setting in motion a cytokine cascade, whereby the initial cytokines released promote more and more cytokine production. The inventor reasoned that as large amounts of cytokines accumulate, systemic side effects ultimately occur. These findings lead to the administration of cytokines in doses that bind only to a fraction of the cytokine receptors, promoting regulatory effects, but without producing toxic symptoms. Accordingly, knowing the affinity of any cytokine in binding its receptor, the fraction of receptors occupied by the cytokine may be calculated, thereby adjusting the cytokine dose accordingly. The effects of the present agents at their respective receptors have been found to be dose-dependent, and to correlate to their binding affinity to the different receptor classes expressed by different types of cells. For example, in the case of IFN-γ, the affinity of the IFN-γ receptor (IFN-γ R) is about $10^{-10}$ M. The concentration of IFN-γ binding these receptors, therefore, can be expected to range from about $10^{-11}$ to $10^{-9}$ M. In similar manner, the teachings provided herein may be applied to the other cytokines and their receptors.

In the case of IL-2, the high affinity receptor class, comprising three peptide chains (α, β, γ), is expressed by antigen-activated T- and B-cells (about $10^7$ cells in the circulation), and by about 10% of the NK cells (total circulating about $10^8$ cells). This receptor class is characterized by a very high affinity for IL-2, as expressed by an equilibrium dissociation constant (Kd) of about $10^{-11}$ M. Accordingly, the inventor reasoned that IL-2 concentrations of about $10^{-12}$ M to $10^{-10}$ M will bind to this class of IL-2R to different degrees. A second class of functional IL-2Rs is comprised of only β and γ receptor chains, and has a 100-fold lower affinity for IL-2 than the high affinity receptor. This intermediate affinity receptor has a Kd of about $10^{-9}$ M, and is expressed by the majority (>90%) of NK cells (about $10^9$ cells). Thus, IL-2 concentrations which are expected to bind this class of receptors range from about $10^{-10}$ to $10^{-8}$ M. The third class, a low affinity receptor, comprises only α peptide chains, and has the lowest affinity for IL-2, with a Kd about $10^{-8}$ M. In this case, the IL-2 concentrations which are expected to bind to this class of receptor range from about $10^{-9}$ M to $10^{-7}$ M. Although target cells that express only α chains have not been identified, α chains have been detected in the serum as soluble IL-2Rs. However, due to their low IL-2 binding affinity, the soluble low affinity IL-2Rs cannot compete effectively with the cellular high affinity IL-2Rs. Some of the characteristics of the three classes of receptors are shown in Table 3 below.

TABLE 3

| | IL-2 Receptor Classes | | |
|---|---|---|---|
| | High (M) | Intermediate (M) | Low (M) |
| Affinity (Kd)* | $10^{-11}$ | $10^{-9}$ | $10^{-8}$ |
| Comp. (Chains) | α, β, γ | β, γ | α |
| Cell Distribution | Activated T & B, ~10% NK | ~90% NK | — |
| IL-2 Conc. | $10^{-12}$ to $10^{-10}$ | $10^{-10}$ to $10^{-8}$ | $10^{-9}$ to $10^{-7}$ |
| No. Responsive Cells | ~$10^8$ | ~$10^9$ | — |

*Kd = equilibrium dissociation constant

The cytokine concentration, the density of cytokine receptors on the cell surface, and the duration of the cytokine-receptor interaction are three important parameters in the regulation of lymphocyte proliferation and differentiation by each cytokine. A finite number of cytokine-receptor interactions must occur before a cell irrevocably commits to responding by proliferating.

In accordance with this invention, the behavior of all cytokines follows a similar pattern. Thus, the % receptors occupied is dependent on the binding affinity of the receptor for the cytokine. The biological response is, thus, ultimately dependent on the concentration of the cytokine and the density and distribution of the cytokine receptor. For example, in normal individuals the vast majority of circulating T and B lymphocytes, i.e., greater than about 99.9%, do not express IL-2Rs and are, thus, IL-2 unresponsive. By comparison, all NK cells express IL-2Rs constitutively, with less than about 10% of NK cells (about $10^8$ cells) expressing high affinity IL-2RS and > about 90% of circulating NK cells (about $10^9$ cells) expressing intermediate affinity IL-2 Rs. The present inventor has shown that over a prolonged period of time, blood concentrations of about $10^{-12}$ to $10^{-10}$ M IL-2 binding to high affinity IL-2Rs, are therapeutic. In addition, he has also found that blood IL-2 concentrations in excess of about $10^{-10}$ M, which bind and activate intermediate affinity IL-2Rs expressed by as many as about $10^9$ NK cells, are toxic. Although exemplified for IL-2 itself, suitable doses for all agents in accordance with this invention may be calculated as follows.

Calculation of % Cytokine Receptors Occupied by Different Agent Concentrations

Knowing the value of the equilibrium dissociation constant (Kd) of each class of cytokine receptors for a binding agent, it is possible to calculate receptor occupancy using the following formula.

$$\% \text{ Receptors Occupied } (\% \ R \ occ.) = \frac{[\text{Agent}] \times 100}{[\text{Agent}] + Kd}$$

For example, at a blood concentration of the agent of about $10^{-11}$ M, which is equivalent to the Kd of the high affinity receptors, 50% of high affinity cytokine receptors will be occupied, as may be seen from the following.

$$\% \ R \ occ. = \frac{10^{-11} M \times 100}{10^{-11} M + 10^{-11} M} = 50\%$$

It thus follows that a blood agent concentration of about $10^{-10}$ M will lead to about 90% occupancy of high affinity cytokine receptors, as is shown below.

$$\% \ R \ occ. = \frac{10^{-10} M \times 100}{10^{-10} M + 10^{-11} M} = 90\%$$

However, the same blood concentration of the agent will occupy only about <10% of the intermediate affinity cytokine receptors, which have an affinity constant which is 100-fold lower (Kd=$10^{-9}$ M) for the cytokine receptor, as may be seen below.

$$\% \ R \ occ. = \frac{10^{-10} M \times 100}{10^{-10} M + 10^{-9} M} = 10\%$$

Similar calculations may be undertaken for different blood concentrations of the agent and other agents and their respective Kds for all receptors incorporated into the equation, as shown above.

Determination of Agent's Toxicities Based on % Receptor Occupancy

The WHO toxicity grades produced by cytokine receptors were estimated from the above calculations, in accordance with this invention, and are shown in Table 4 below. They are based upon the World Health Organization (WHO) toxicity grading scale, shown in Table 2 above. Similar estimates may be done as taught herein for all the other agents of this invention.

TABLE 4

Prediction of Agent's Toxicities

| WHO Toxicity Grade | Agent Plasma Concentration (M) | Receptor Occupancy (%) | |
|---|---|---|---|
| | | High Aff. Rec. | Intermed. Aff. Rec. |
| 0 | $10^{-11}$ | 50 | 1 |
| 1 | $10^{-10}$ | 90 | 10 |
| 2 | $10^{-9}$ | 99 | 50 |
| 3 | $10^{-8}$ | 99.9 | 90 |
| 4 | $10^{-7}$ | 99.99 | 99 |

Calculated utilizing a Kd = $10^{-11}$ M for high affinity receptors, and a Kd = $10^{-9}$ M for intermediate affinity receptors.

Thus, in accordance with the inventor's reasoning, which lead to the invention, the severity of the toxicity is directly related to the agent's blood concentration. The latter, thus, together with the Kd value for the ligand-receptor interaction, may be used to calculate the degree of receptor occupancy as described above. If the Kd for the specific ligand-receptor (agent-receptor) is not known, it may be determined as described above or by other methods known in the art. Thereafter, using the above table, and having measured the peak plasma concentration of the agent occurring, for example, about 2 hours after a subcutaneous injection of the agent, the practitioner may adjust, for example, the dosage of cytokine receptors for each individual subject. For example, if a given dose yields a peak plasma concentration of about $2 \times 10^{-10}$ M, using the above formula, it can be calculated that this concentration will lead to about 95% occupancy of high affinity cytokine receptors, and more than about 16% intermediate affinity receptors. The dose, therefore, should be reduced gradually to that expected to saturate less than about 90% high affinity cytokine receptors and less than about 10% intermediate affinity cytokine receptors.

Ligand-Receptor Binding Assay

The ligand-receptor binding assay may be conducted, for the different agents in accordance with this invention, as described by Robb et al. (Robb, R., Munck, A., and Smith, K. A., J. Exp. Med. 154: 1455–1474 (1981)). In brief, a cytokine such as IL-2, IL-12, IL-15, IFN-, IFN-β, IFN-γ, the CD-40 ligand, or any other ligand (agent) in accordance with this invention, must be in their native configuration, and substantially free of contamination by other molecules. The ligand or agent may be labeled, for example, using radioisotopes, enzymes, and other markers. Target cells, isolated membranes, cytoplasm, or nuclei, may then be mixed together with the labeled ligand, and the ligand and receptor allowed to reach a steady state, where the rate of association of the ligand with the receptor about equals the rate of dissociation of the ligand from the receptor. Subsequently, any unbound ligand or agent may be separated from the receptor-bound ligand or agent, usually by centrifuging the bound ligand or agent, and the amounts of the bound and unbound ligand or agent measured, e.g., as described by Robb et al. (Robb et al., J. Exp. Med. 154: 1455–1474 (1981)). The affinity of the ligand-receptor interaction (Kd) may be calculated, as well as the number of receptors per cell, or per weight of cytoplasm or nuclei, from these two experimentally determined values, knowing the number of cells, or amount of membranes, cytoplasm, or nuclei, used. The data may be plotted by the method described by Scatchard (Scatchard, Ann. NY Acad. Sci. 51: 660–672 (1949)). The ratio of bound vs. free ligand or agent may be plotted on the y-axis and the amount of bound ligand or agent on the x axis. The slope of the data points yields the Kd (x/y), whereas the x-axis intercept yields the number of receptors. Knowing the equilibrium dissociation constant (Kd), the % receptors that will be occupied at each ligand or agent concentration may be calculated as described above.

The dose range of agent prescribed herein activates the immune system in a patient without being toxic, thus permitting the subject to carry out normal daily activities. For example, asymptomatic HIV individuals are able to self-administer daily doses of agent in accordance with this invention, safely and without toxicity, for prolonged periods of time. The present immunotherapy is effective and free of toxicity WHO grade 1 or higher, for periods greater than about 6 months or 1 year, and even for longer periods of time, without producing systemic side effects or significant laboratory abnormalities. Different preparations of a specific cytokine or related agent, and different formulations may require varied daily doses, which depend on the agent's binding constant to the respective receptors, and the existence and number of different kinds of receptors they selectively bind to. Significant stimulation of the immune system, however, is evidenced by substantial increases in circulating leukocytes, such as NK cells, eosinophils, monocytes, and/or CD+4 T-cells, among others. More generally, the present immunotherapy may be extended for about one or two years, and even longer periods, or be administered continuously as a maintenance therapy, for example, to those individuals suffering from a congenital or acquired immunodefficiency, chronic inflammation, etc.

Some of the toxicities which are monitored to determine a suitable dosage for the agent utilized in the studies include weakness, fatigue, lethargy, myalgia, and low grade fever. These symptoms usually occur within a few days after beginning the agent's administration. When toxicity is observed during a trial, therapy should be immediately stopped, and the patients placed on a lower daily dose of the agent. If necessary, this procedure is repeated until a safe dose is found. No toxicities to major organ systems are detected by laboratory assays throughout the full period of the tests. All patients are, therefore, able to perform the self-administration of the agent daily, while conducting normal activities without any hindrance associated with side effects brought about by the treatment.

For individuals infected with viral infections, such as HIV, the low dose of the agent administered in accordance with this invention does not trigger a burst in viral production (of HIV), as reported previously upon i.v. administration of high IL-2 doses. For example, persisting increases as high as 50-fold in plasma HIV levels were reported in the prior art after the daily administration of $4 \times 10^6$ to $12 \times 10^6$ $IU/m^2$ IL-2 for 5 days. In accordance with this invention, an increase in viral production of that magnitude is due to the presence of pro-inflammatory cytokines, which are also responsible for the toxic symptoms observed after administration of high doses of cytokines. By way of comparison, the present immunotherapy utilizes about 50-fold lower daily doses of some cytokines, e. g., IL-2, than those utilized by the prior art. The present doses result in insignificant or no increases in plasma levels of virus when compared with pre-treatment levels. Further yet, no opportunistic infections or malignancies are observed in any of the individuals receiving the low agent's doses of this invention.

The substantially lower cytokine doses utilized herein, when administered continuously, stimulate the immune system, and significantly increase the number of circulating NK cells, eosinophils, monocytes, and/or CD4+ T cells, among others. When, prior to this invention, high doses of cytokines, such as IL-2, were administered by others i.v. intermittently every 2 months, only transient increases in CD4+ T cells were observed after each injection, while the number of circulating NK cells, eosinophils, and monocytes were observed to remain unchanged.

The continuous administration of agent, such as IL-2, IFN-$\beta$, IFN-$\gamma$, the CD-40 ligand, IL-15, and the like, in accordance with the invention, also elicits a progressive accumulation of circulating CD4+ T-cells. In contrast, the prior art showed that the intermittent administration of high doses of IL-2, leads to only a transient increase in CD4+ T-cell counts in 6 out of 10 subjects. Based on a mean monthly gain in CD4+ T-cells/mm$^3$ observed in the 6-month study with IL-2 reported hereinbelow, an increase of greater than about 300 cells is likely in the CD4+ T-cell count throughout a whole year of therapy. In comparison, prior art reports show that when the antiviral agent zidovudine (250 mg, 4 times daily) was administered, the monthly rate of increase in CD4+ T-cells during 6 months of treatment was only 4 cells/mm$^3$ (Seligmann et al. The Lancet 343:871–81 (1994)) versus an increase of about 28 cells/mm$^3$ observed when IL-2 was administered by the present method. Combining ziduvudine with lamavudine (3TC) augments the rate of increase of CD4+ T-cells to about 10 cells/mm$^3$/month, and the three drug combination of zidovudine, lamovudine, and indinovir was recently found to increase the CD4+ T-cell count by about 20 cells/mm$^3$/month.

The present invention, thus, provides a novel and effective method of stimulating and/or inhibiting the immune system of a subject by administering to a mammal, including a human, a daily dose of an agent having cytokine activity, such as natural and recombinant cytokines, active fragments, pharmaceutically acceptable analogues, and derivatives thereof, mixtures thereof, or mixtures with one or more agents having other therapeutic activity, effective to activate the respective high affinity cytokine receptors without eliciting substantial toxicity WHO grade 1 or higher.

"Cytokines" are defined herein as any agent produced by cells in response to external stimuli, such as microbes or microbial toxines that interact with other cells by means of specific high affinity receptors, analogues and derivatives thereof. Examples of cytokines are IL-2, 3, 4, 5, 6, 7, 9, 10, 11, 12, 13, 14, and 15, from the interleukin family, the tumor necrosis factor (TNF) family, which includes TNF-$\alpha$, TNF-$\beta$ (lymphotoxin), nerve growth factor (NGF), and the CD40, Fas, CD27, and CD30 ligands, the interferon (IFN) family, which includes IFN-$\alpha$, IFN-$\beta$, and IFN-$\gamma$, the chemokine family including IL-8, macrophage inhibiting protein (MIP), and Rantes, and the like. This invention encompasses all known forms of natural and recombinant cytokines, their active fragments, pharmaceutically acceptable analogues and derivatives, and their mixtures.

Various forms of the composition are provided herein for administration of the agent of the invention under the conditions prescribed herein. One of them is a systemic composition, also comprising a diluent and/or carrier for system administration, and optionally other bioactive agents and additives which are described below or standard in the art. This form may be in the form of a solution, suspension, powder, tablet, an emulsion, and encapsulated particles, among others, or mixtures or combinations of these forms. The agent may be present in the systemic composition in an amount of about 0.0001 to 50 wt % of the composition, more preferably about 0.1 to 30 wt %.

Another form is a topical composition, which in addition to the agent comprises a carrier or diluent for the agent, which is suitable for its transdermal delivery and optionally one or more of a variety of agents suitable for the preparation of different formulations, which will be selected in accordance with the type of formulation and route of administration desired. Examples of these ingredients are buffers, salt forming acids and bases, perfumes, colorants, emollients, adjuvants, single or multiple enteric coatings, copolymers, microporous or semi-permeable membranes, enzyme inhibitors, mucoadhesives, chelating agents, particulate systems, viral envelope proteins, liposomes and other micelles, emulsifiers, lipoproteins and other fatty acid derivatives, surfactants, bile salts, hydrophilic, neutral, and hydrophobic polymers and co-polymers, hydrogels, biodegradable polymers and co-polymers. The composition may also contain additional bioactive agents such anti-bacterial, anti-viral, anti-fungal, anti-parasitic, anti-metabolic, anti-inflammatory, vasoactive, anti-neoplastic, bronchodilating, local anesthetic, immunomodulating, growth promoting and regenerating agents, enzymatic, hormonal agents, neurotransmitters, and cell receptor proteins and ligands. This composition may be in the form of a cream, an ointment, a solution, a gel, a powder, a suspension, an emulsion, encapsulated particles, or mixtures or combinations of these forms. The agent may be present in different amounts, typically the dermal composition has about 0.001 to 50 wt % or more, and preferably about 0.1 to 30 wt %. However, other amounts larger and smaller are also suitable. Another preferred form of the composition is in the form of a controlled release composition wherein the formulation ingredients added control the rate of release of the agent. These may be degradable polymers and copolymers, matrixes which "leach out" the agent, and the like, as is known in the art.

The additional ingredients, which are optionally present in the composition are generally utilized in amounts standard in the art, except when an additional ingredient may have activity similar to that of the agent, the respective doses may adjusted to account for this factor. This is also the case, when more than one cytokine is present in the composition, e.g., when IL-2 and another agent having IL-2 activity are added to the composition. The latter may be incorporated into any and all the compositions of the inventions as taught by the art at large. Preferred, however, are amounts which have a beneficial therapeutic activity without causing toxicity WHO grade 1 or higher.

The composition may be produced in the form of an implant for releasing a desired amount of the agent over a pre-determined period of time. Any and all compositions in accordance with the invention may also be provided as a kit, along with instructions for its use, particularly in terms of the any necessary manipulations, the number, frequency, and timing of administrations or applications, the form or area of the body to be applied to, taking into consideration different body surface area and weight of the subject. This is particularly important when it is applied or administered to children, particularly infants and newborn babies, the infirm, and the elderly, as well as to small and large animals. Smaller or larger doses may be required in these cases.

The composition may be delivered from a passive transdermal delivery device formed from a solid support with a compartment containing a solution or suspension comprising the composition. The compartment has a permeable side which is applied to an area of a subject's skin or dermis and the agent is allowed to pass from the device onto and through the skin, mucosal, or buccal surfaces of the subject. The device is preferably placed in a sealed sterile container immediately after manufacture by methods known in the art. A removable cover may be placed on the permeable side of the container prior to sealing and/or packaging to retain the solution or suspension of the agent during storage and prior to use.

This device may be in the form of an electrotransport device which also contains donor and counter electrodes, an external power source and control circuitry. This device may also be in the form of ultrasound device also containing an ultrasound generator or transducer, an external power source, and control circuitry. Such devices are known in the art and need not be further described herein. The solution or suspension containing the agent requires the presence of electric conducting agents which will aid in the transport of the electrical current which facilitates the passage of the agent from the solution onto the skin or dermis and through it. In the case of protein such as the present agent, it becomes important to provide means of administration that will not degrade or hydrolyze the peptic bonds, in order to preserve the activity of the agent. In this respect, the topical application of the agent in the form of a multiplicity of formulations is ideally suited to avoid the hydrolyzing conditions of the gastrointestinal tract while providing a direct passage, after the agent is absorbed through the skin or mucous tissue, directly into the blood stream.

A useful form of the invention is a unit dosage composition, which may be packaged in a sterile container, having sufficient amounts of one or more forms of the agent to maintain a therapeutic level in blood for a period of about 24 hours. This amount of the agent to be administered may be calculated as described above for each individual agent, and in a similar manner when the composition comprises more than one agent, the relative concentrations may be utilized, as well. Examples of agents in accordance with this invention are natural and recombinant cytokines, fragments, fusion proteins, PEG, carbohydrate, lipid, therapeutic agent, reduced, non-glycosylated, and mutated derivatives thereof, although others are also contemplated herein.

When IL-2 is utilized, the daily dose should be adjusted for the agent of the invention, if the agent either binds to the high affinity IL-2 receptors, or if the agent's activity produced by some other means elicits secondary and/or tertiary events similar to those produced by IL-2 on the immune cellular system. Examples of secondary and tertiary effects are the release of secondary or tertiary cytokines. Given that 1 pmole IL-2 is equivalent to about 250 IU, preferred daily doses of IL-2 are about 15,000 and lower, to about 1,500,000 IU and higher, preferably up to about 1,000,000 IU, more preferably up to about 750,000 IU, and still more preferably up to about 500,000 IU, and as low as about 20,000 IU, preferably as low as about 50,000 IU, and still more preferably as low as about 60,000 IU, and equivalent amounts of its pharmaceutically acceptable analogues and derivatives thereof, or mixtures thereof. Examples of agents having IL-2 activity are natural and recombinant IL-2, its fusion proteins, and PEG, carbohydrate, lipid, therapeutic agent, reduced, non-glycosylated, and mutated derivatives thereof, although others are also contemplated herein.

As with IL-2, where a dose of about 1,000 pmole/m$^2$ yields a peak plasma concentration about 20 pM 2 hours after a subcutaneous injection, it can be advanced that the other cytokines, having similar molecular characteristics and acting on their receptors, will behave similarly. For example, the interleukin family of cytokines are all of similar size, about 10 to 20 kDa, and molecular arrangements (four antiparallel helices). The maximum non-toxic dose will, therefore, be about 500 to 2,000 pmoles/m$^2$/day for the members of this family having a dissociation constant of their respective receptors of about 10 pM. IFN-γ is an example of another important group of immunoregulatory cytokines, the equilibrium dissociation constant of the IFN-γ R being about 100 pM. IFN-γ is similar to IL-2 in size (about 17 kDa), but the affinity for its receptor is about 10-fold lower than that of IL-2. Therefore, about 10-fold higher doses of IFN-γ are necessary, about 5,000 to 20,000 pmoles, to obtain plasma concentrations effective to saturate most IFN-γ R. TNF is yet an example of another important immunoregulatory family of cytokines. This cytokine family is generally composed of members with trimeric structures, where each monomer is about 17 kDa. A dose of the trimer similar to the IL-2 dose, about 500 to 2,000 pmole, would produce a plasma concentration of the cytokine of about 20 pM. Given that the Kd of the TNF receptor is about 100 pM, an about 10-fold higher dose of TNF is necessary to achieve therapeutic plasma concentrations. These ranges are approximate calculations, and more specific ranges may be calculated for individual cytokines utilizing their specific characteristics and binding constants as described above.

The unit dosage composition may be prepared in a variety of forms for the delivery of the agent. Examples are powder, tablet, capsule, dragee, cream, solution, suspension, emulsion, gel, spray, or liposomal or other micellar forms. Preferred are solid, particularly freeze-dried, and liquid forms. Also preferred are other forms such as those suitable for injection, topical application, controlled release products, inhalation, and others. Examples of controlled release products are transdermal and intradermal devices, slow release oral formulations, patches, skin, mucosal and transbuccal implants, suppositories, and the like. Implants are preferred for long term delivery of the agent. Controlled release products may be prepared as is known in the art and designed for releasing desired amounts of the agent over a pre-determined period of time. In most instances, the amount of the agent contained in the control release product is substantially higher than the desired daily dose. In some cases, the product may contain sufficient amounts of agent for releasing a daily dose over a period of days, weeks, months, and even years. The product may be tested, and the amount of agent to be released adjusted in accordance with the observed absorbed dose. Given that 1 pmole IL-2 is about 250 IU, the daily dose of IL-2 administered is preferably about 15,000 to up to about 1,000,000 IU/m$^2$ body surface. The upper daily dose limit is preferably not higher than about 900,000 IU/m$^2$, still more preferably not higher than about 800,000 IU/m$^2$, and even more preferably not higher than 450,000 IU/M$^2$. The lower limit for the daily dose is preferably no lower than about 30,000 IU/M$^2$, more preferably no lower than about 45,000 IU/M$^2$, and even more preferably not lower than about 100,000 IU/m$^2$. However, the slow release of higher or lower amounts of the agent are also contemplated herein. Any of the forms for administration of the agent may also contain other formulation components and additional bioactive agents as described herein.

The agent of this invention may also be administered from an inhalant device, including those utilized to introduce therapeutic or preventative agents into the lungs, as is the case of transpulmonary administration to asthmatic patients. Such devices are known in the art and available commercially. All types of products and compositions which are part of this invention may be provided as a kit, and preferably as a self-administration kit, primarily comprising, in separate sterile containers, a number of unit dosage compositions, and detailed instructions for use of the kit, and optionally, one or more devices including syringes and needles, transdermal, transbuccal, or intradermal patches or implants, or inhalators, for delivering the agent, and a carrier diluent. These devices may be placed in sterile containers, and the entire kit may be contained in a case for marketing and distribution.

The compositions and products provided herein may all be utilized for stimulating and thereafter maintaining the stimulation of the immune system of a mammalian animal by chronically administering the agent of the invention in the form of a composition over a prolonged period of time in an amount effective to activate the high affinity cytokine receptors, including the IL-2, IFN-γ, IFN-β, and IL-12 receptors, without eliciting any substantial toxicity WHO grade 1 or higher. The present inventor, for the first time, found a manner to stimulate and/or inhibit, and maintain the stimulation or inhibition of the immune system of a mammalian animal, e.g., a human, without interfering with his/her normal activities or producing undesirable side effects which lower the quality of life of the individual. The present immunotherapy may be administered for six months, one year, and for periods in excess of these times as long as medical parameters, including systemic symptoms of fatigue, malaise, myalgia, fever, and other symptoms, typical of over-stimulation of the lower binding constant, intermediate and low affinity receptors, are monitored. In general, the combined amount of agent (s) administered should be effective to produce about 10 to 90% and greater saturation, preferably about 20 to 85%, more perfectly about 30 to 80%, and still more preferably about 50 to 70%, and in some cases below about 60% of the high affinity IL-2 receptors. However, in some cases, no toxicities are elicited even at agent occupancy greater than about 93%, and even about 95% and higher. This is generally attained through a dose of about 15,000 to 1,000,000 IU IL-2/m$^2$ body surface/day, when the IL-2 is administered alone. The composition of the invention may be administered by topical and systemic routes, including subcutaneous, intramuscular, intradermal, intralymphatic, intratumor, transdermal, intradermal, intracavitary, oral, intranasal, intravaginal, intraanal, intrabuccal, transbuccal, transpulmonary, or sublingual routes, or by inhalation or implant. Typically, the implants may be placed in the following areas: the limbs, thorax, abdomen and back, and the topical application, particularly when administered by means of a device, may be typically applied to the same areas.

The present immunotherapy may be applied as a preventative or therapeutic treatment to a variety of conditions. At no time in the past have IL-2, IFN-α, IFN-β, IFN-γ, the CD-40 ligand, IL-15, IL-12, or any of the other agents disclosed herein having cytokine activity, been utilized to boost or inhibit the immune system of normal animals or humans, including children. The present technology may be utilized in humans as well as all types of mammalian animals, including equines, bovines, ovines, large and small animals in the care of a veterinarian, and animals found in the wild, among others. In fact, the present invention extends to the preventative administration of the agent to normal subjects, for example in cases of travel to areas of the country or the world affording the possibility of a contagious infection, and even in the case of the common cold or flu that afflicts many people during the winter months. The present immunotherapy is also applicable to the prevention and treatment of viral, bacterial, fungal and parasitic infections in general, congenital or acquired immunodeficiencies, inflammation, necrosis, sepsis, and cancers or other malignancies such as carcinomas, melanomas, sarcomas, leukemias, lymphomas, and myelomas, as well as a vaccine adjuvant, among others. In many instances, immunotherapy with the agent of the invention prevents increases in malignant cell mass or count, and in some instances, it even produces a reduction in tumor mass.

Other parameters that may be monitored in order to adjust the dose of the agent administered daily are the blood cell count of circulating lymphocytes, monocytes and polymorphonuclear leukocytes, such as T-cells, B-cells, NK cells, monocytes, eosinophils, neutrophils, basophils, antigen-presenting cells, among others. In the case of viral infections, particularly in the presence of the human immunodeficiency virus, one of the ways to determine an adjustment in the dose administered to an individual is to monitor the count of circulating microorganisms. The present immunotherapy does not increase the count of circulating virus or other opportunistic microorganisms when administered over a prolonged period of time, and in some cases it even decreases their count. When the immunotherapy is applied to subjects afflicted with cancer, it is useful to monitor the size of the malignant cell mass or count. This therapy may be administered as the main cancer therapy in the indicated types of malignancies or after surgery, chemotherapy or radiotherapy. In the case of HIV+ or AIDS patients, the present immunotherapy may encompass, in addition to the agent, nucleic acid analogues, other anti-viral drugs, and enzyme inhibitors, in amounts known in the art. Particularly preferred are formulations containing one or more anti-viral agents of the nucleic acid analogue class and one or more protease inhibitors. More generally, the present therapy may be utilized in conjunction with the administration of vaccines, such as hepatitis B and C vaccines, and the like, as an adjuvant. The agent may be administered in the same formulation with these agents or by a different route. Different drugs may be alternated while the agent of the invention is administered over a prolonged period of time. When specific drugs for which there is no established dose in the art are combined, the combined immunotherapy in accordance with this invention should be started by lowering the dose of each individual drug and then progressively increasing their doses one at a time while monitoring the effect produced on one of more of the parameters followed, as described above. An artisan with average skill in the art of medicine or veterinary science would know how to proceed to attain a desirable combination dose.

In one preferred mode, the agent may be self-administered by the human subject, preferably subcutaneously, transdermally, intrapulmonarily, transbuccally, or by implant. However, for specific types of patients or applications other forms are also preferred. The present treatment is suitable for application to a variety of conditions, which benefit from the stimulation and/or inhibition of the immune system. For example, the administration of low doses of the agent of this invention, as described herein, produces an increase in one or more of a group of circulating immunity-building cells, such as lymphocytes, monocytes and polymorphonuclear lymphocytes, including T-cells, particularly CD4+ T-cells, B-cells, natural killer (NK), eosinophils, monocytes, basophils, and antigen-presenting cells. One specific type of recombinant IL-2 has now been shown, in a clinical trial described below, to enhance the concentration of, for example, circulating NK cells, monocytes, eosinophils and CD4+ T-cells.

Each cytokine, which is a member of the cytokine group described in this application, may be utilized individually, as one preferred embodiment. In addition, parings of one or more cytokine from each of the four listed groups may be utilized in a composition, which is also one preferred embodiment. Still another preferred embodiment are compositions comprising 2, 3 and more of the IL-2 to 15 interleukins, above or in combination with other cytokines, antivirals, anti-inflammatories, etc. Still another preferred embodiment is a composition comprising one or more of the interluekins with one or more tumor necrosis factors (TNFs). Still another preferred embodiment is a composition comprising one or more members of the TNF family, such as a TNF-α, NGF, and one or more of the ligands, and one or more members of the interferon or interleukin families. Still another preferred embodiment is a composition comprising a member of the chemokine family such as IL-8, MIP or Rantes, and one or more members of one of the other families. Although not specifically listed herein, all combinations of different cytokines, their fragments, analogues and derivatives, and mixtures thereof, are also preferred.

All compositions may further comprise one or more antiviral agents. Suitable anti-viral agents are any of the agents utilized in the treatment of viral infections. Examples are zidovudine (AZT), 2',3'-dideoxyinosine (ddI), 3'-azido-2',3'-dideoxythymidine, acyclovir, 1,3-dihydro-2-propoxy-methyquanine (gancyclovir), ribavirin, dideoxycytidine (ddC), lamivudine (3TC), enzyme inhibitors, such as protease inhibitors, e. g., sequinovir, ritonavir, and indinovir, among others, and combinations thereof in twos, threes, and higher numbers. Preferred are combinations of one or more nucleic acid analogues and one or more protease inhibitors with one or more cytokines. Still more preferred is one or more cytokine(s) and three antiviral compounds, such as 3TC, acyclovir, ritonavir, sequinovir, and indinovir, among others. The anti-bacterial agent may be any one agent known to be effective against the agent associated with the infection. Examples are pentamidines, trimethoprim-sulfamethoxazole, sulfonamides, penicillins, cephalosporins, aminoglycosides, tetracyclines, chloramphenicols, and combinations thereof. Any specifically targeted antibodies and their fragments are suitable for use herein to deliver molecules attached to them to specific sites. Examples are radioisotope, enzyme, toxin, and other therapeutic agent-carrying monoclonal antibodies, and combinations thereof. Any anti-fungal agent is suitable for use herein. Examples are flucytosine, amphotericin B, fluconazole, griseofulvine, and combinations thereof. Any anti-parasitic agent is suitable for use herein. Examples are pyrimethamine, quinacrine, thiabendazole, levamisol, and combinations thereof. Any anti-metabolic agent may be utilized herein. Examples are purine analogues, folic acid analogues, pyrimidine analogues, and combinations thereof. Any anti-inflammatory agent is suitable for this invention. Examples are steroidal anti-inflammatory agents, non-steroidal anti-inflammatory agents such as acetaminophen and aspirin, and combinations thereof.

In addition, vasoactive agents such as epinephrine, norepinephrine, dopamine and combinations thereof, vaccines such as hepatitis B and C vaccines, bronchodilating agents such as $\beta_2$ receptor agonists, and combinations thereof, local anesthetic agents such as procaine, cocaine, and combinations thereof, growth promoting and regenerating agents such as epidermal growth factor, fibroblast growth factor, and combinations thereof, additional lymphokines or cytokines such as interleukins other than IL-2, interferons, and the like, hematopoietins, growth factors, hormones, chemokines, active analogues, fragments, fusion proteins and pharmaceutically-acceptable derivatives thereof, and combinations thereof, agents such as soluble CD4 and analogues thereof, anionic polysaccharides, and anti-neoplastic agents such as alkylating agents, anti-metabolites, hormones, vinca, alkaloids, anti-proliferative agents, and combinations thereof. Other bioactive agents of similar or different activities and applications are also encompassed. All biological agents are either commercially available or may be prepared by methods known in the art.

Having now generally described the invention, the same will be better understood by reference to certain specific examples, which are included herein for purposes of illustration only, and are not intended to be limiting of the invention or any embodiment thereof, unless so specified.

EXAMPLES

Example 1

Preparation of IL-2 for Administration

Recombinant human IL-2 (R-Met-HU IL-2 (Ala 125 or rIL-2) was obtained from Amgen (Thousand Oaks, Calif.). Each 2 ml vial contained approximately 0.4 mg/ml of recombinant IL-2 (rIL-2) in 1.1 ml $H_2O$. The rIL-2 used for the study had a specific activity of $9\times10^6$ units/mg protein. All dosages for the study were calculated as International Units (IU), using a specific activity of $15\times10^6$ IU/mg protein. Therefore, 1 pmole IL-2 is about 250 IU.

Each vial was diluted to 50% strength with 5% dextrose in water. All individuals in the study received the rIL-2 daily dose in pre-measured syringes, which were kept refrigerated until use.

Example 2

Profile of Patients Selected in IL-2 Trial

Individuals over the age of 18 were eligible for enrollment in the trial if they tested positive for HIV-reactive antibodies, if they were HIV p24 antigen negative, and if they had no concurrent opportunistic infections. In addition, the criteria for eligibility included an absolute CD4+ T-cell count of between 200 and 500 cell/mm$^3$ and being on nucleoside-analogue antiretroviral medication (e.g. AZT, 3TC, ddI, d4T) for at least one month prior to starting IL-2 therapy.

Any individual that had any chronic illness unable to be controlled by medication, pregnant or nursing, or had any history of malignancy was excluded. Hematologic and biochemical criteria utilized for excluding individuals included: total bilirubin >5 times normal, AST >90 IU, creatinine >2.0 mg/dl, neutrophils <100/mm$^3$, hemoglobin <10 mg/dl, platelets <75,000/mm$^3$.

14 individuals were enrolled, who had a mean age of 37 years (range 28–48). The mean time of known HIV infection prior to entrance in the study was 7 years. Before initiation of IL-2 therapy, the mean CD4+ T-cell count was 338 (range 202–495). The group was homogeneous with respect to leukocyte and differential counts, and there were no differences in these parameters among the subjects who were given different IL-2 doses. Twelve of the 14 individuals enrolled had been taking anti-retroviral nucleoside analogue medication for at least 3 months. Two subjects began anti-nucleoside medication 6 weeks prior to initiation of IL-2 therapy.

Based upon an expected rate of decrease of about 80 CD4 T-cells/mm$^3$ per year, the individuals are expected to lose on the average 40 cells/mm$^3$ over a period of six months.

Example 3

Initiation of 6-month Clinical Trial

On the first day of therapy, all individuals participating in the study were admitted to the hospital. Each individual was given the initial subcutaneous injection of IL-2 and, then, frequent blood samples were taken for the first 24 hours for IL-2 to conduct pharmacokinetic studies. All subjects then received instructions on the self-administration of IL-2 by subcutaneous injection, and were seen subsequently on an out-patient basis weekly for 6 weeks, and then biweekly for the 6 month study period.

Example 4

Doses and Regimes for 5 Dose Groups

Group 1: 125,000 IU rIL-2/m$^2$/day (500 pmole/m$^2$/day)

Six individuals self-administered 125,000 IU (8.3 µg) rIL-2/m$^2$/day. Two of the individuals had medical histories of mild allergic asthma, and an increase in severity of their asthma symptoms was correlated with each IL-2 inoculation. Therefore, the administration of IL-2 was stopped, and the cessation of IL-2 therapy resulted in the attenuation of symptoms. Subsequently, the IL-2 dose was reduced by 50% for these 2 individuals to 62,500 IU (4.15 µg) rIL-2/m$^2$/day. The other 4 subjects, receiving 125,000 IU (8.3 µg) rIL-2/m$^2$/day, completed the course (6 months) of therapy without any detected toxicity.

Group 2: 62,500 IU rIL-2/m$^2$/day (250 pmole/m$^2$/day)

Two individuals self-administered 62,500 IU (4.15 µg) rIL-2/m$^2$/day for 6 months (see, Group 1). Although the 2 individuals had side effects at a higher dose, (125,000 IU), no recurrence of the asthma symptoms was observed at this does, and the individuals completed the study without untoward effects.

Group 3: 250,000 IU rIL-2/m$^2$/day (1,000 pmole/m$^2$/day)

Eight individuals started self-administration of 250,000 IU (16.7 µg)rIL-2/m$^2$/day.

Two of the 8 individuals experienced fever (38.5° C.), myalgia and fatigue, with the onset of systemic symptoms occurring after 4 to 5 days of inoculation, and 6 to 8 hours after each IL-2 injection. Their dose was, thus, decreased to 187,500 IU (12.5 µg) rIL-2/m$^2$/day. The 2 individuals tolerated the lower dose throughout the 6 months of therapy without any further side effects.

The remaining 6 individuals from Group 3 were administered 250,000 IU (16.7 µg)rIL-2/m$^2$/day, and completed the 6 months of therapy without any significant systemic symptoms.

Group 4: 187,500 IU rIL-2/m$^2$/day (750 pmole/m$^2$/day)

The administration of the drug was stopped in the two individuals experiencing fever, myalgia and fatigue after 4 to 5 days of inoculating 250,000 IU rIL-2/m$^2$/day, and 6 to 8 hours after each rIL-2 injection.

Their dose was decreased to 187,500 IU (12.5 µg) rIL-2/m$^2$/day, and they underwent a full course of self-administration at this dose. These two individuals tolerated the lower dose throughout the 6 months of therapy without any side effects.

Group 5: 500,000 IU rIL-2/m$^2$/day (2,000 pmole/m2/day)

Four subjects received 500,000 IU (33 µg) rIL-2/m$^2$/day IL-2. All the individuals treated at this dose developed systemic symptoms after 4 to 5 days of injections, and were unable to undergo further treatment at this dose level. The treatment was, thus, discontinued.

Example 5

Determination of Toxicity During IL-2 Trial

Toxicity was defined as two consecutive abnormal values found for any one individual. Dose limiting toxicity (DLT) was defined as ≧WHO (World Health Organization) grade 1 toxicity, as shown in Table 2 above. If, and when, DLT occurred in any one individual, treatment was withheld from that particular individual until the toxic symptoms or signs resolved. Treatment was then resumed at an IL-2 dose midway between the previous dose level and the current dose (the dose was halved). The objective was to achieve a dose that was non-toxic but that would permit each subject to carry out normal daily activities.

Example 6

Determination of IL-2 Plasma Concentration

Plasma IL-2 concentrations were determined by ELISA (Endogen, Inc., Boston, Mass.), according to the manufacturer's specification. The lower limit of detection of IL-2 in plasma was 0.5 pM (7.5 pg/ml).

Low, but detectable levels of IL-2 were measurable in 11 of the 14 patients before treatment with IL-2 was started. The mean plasma IL-2 concentration of the samples was 2.5±0.6 pM SEM (range 0.5 to 8.4 pM).

Example 7

Pharmacokinetic Studies for IL-2 Trial

The plasma IL-2 concentrations were determined at frequent intervals for 24 hours following three different doses of the cytokine. At the lowest dose of 125,000 IU/m$^2$, which is equivalent to about 500 pmole, the peak plasma IL-2 concentration of 9+2 pM occurred after 2 hours. By comparison, at 250,000 IU/m$^2$/day (1,000 pmole), the peak plasma IL-2 concentration after 2 hours was 22±2 pM, and a dose of 500,000 IU/m$^2$/day (2,000 pmole) yielded a peak plasma concentration of 35±10 pM.

Example 8

Determination of Circulating Leukocyte Count in Individuals in IL-2 Trial

The determinations of leukocyte types and concentrations were performed by tricolor flow cytometry using monoclonal antibodies directly conjugated with fluorochromes as described by Stewart and Stewart (Stewart, C. and Stewart, S., "Cell Preparation for the Identification of Leukocytes", Darynkiewicz Z., Robinson, J., Crissman H., Eds., in Methods in Cell Biology, pp. 39–60 (1994)).

Example 9

Effect of IL-2 Therapy on Leukocyte Production by Individuals in IL-2 Trial

Six individuals enrolled in the trial received <125,000 IU rIL-2/m$^2$/day, which lead to subsaturating IL-2 levels. Eight individuals received 187,500 IU rIL-2/m$^2$ and 250,000 IU/m$^2$, having near saturating peak plasma rIL-2 levels. The data on leukocyte production obtained from these two groups were analyzed separately and compared with one another.

Over the six month period of treatment, no significant changes were observed in absolute neutrophil counts, CD8+ T-cell counts or B-cell counts from values obtained prior to rIL-2 therapy for either group. Nor were there significant differences in levels of circulating white blood cells between the two treatment groups during therapy.

A marked increase in the mean concentration of circulating NK cells, however, was observed in the group receiving a daily doses of 250,000 IU rIL-2/m$^2$ (Groups 3). After six months of treatment, the NK cell count or concentration had increased 7-fold when compared to the count prior to initiation of therapy. No significant change was observed in the NK cell count in the group that received ≦125,000 IU/m$^2$/day (Group 4).

Linear trends in NK cell counts occurring during the trial period were calculated for each treatment group as a mean of the slopes obtained for each individual subject using data obtained at monthly intervals. A mean monthly gain of 50 cells/mm$^3$ was observed in the group that received 250,000 IU rIL-2/m$^2$/day (Group 3), compared with a mean monthly gain of 9 cell/mm$^3$ for the group that received ≦125,000 IU rIL-2/m$^2$/day (Group 4) (p=0.04).

The concentration of circulating eosinophils was also observed to change. An increased eosinophil count was observed after only 2 weeks of rIL-2 inoculations, and peak levels occurred at 1 month after inoculation, with a subsequent decrease toward baseline within 2 months. There was a greater increase in circulating eosinophils at the 187,500 and 250,000 IU rIL-2/m$^2$/day doses than at the lower doses. Thus, with this rIL-2 preparation, a greater than 9-fold increase in eosinophils occurred at the latter doses after 1 month of therapy, compared with a lesser than 3-fold increase for the subjects receiving the submaximal doses. In addition, at the latter doses, the circulating count of eosinophils reached a steady state that was 2- to 3-fold greater than that observed prior to starting the rIL-2 therapy (t=0). At the lower rIL-2 doses, the eosinophil count returned to baseline without reaching a steady state.

A rIL-2 dose-dependent change in the concentration of circulating monocytes was also observed. At the lower rIL-2 doses (Groups 1 and 2), the monocyte counts decreased slightly during the study interval. By comparison, at the intermediate and higher doses (Groups 3 and 4), there was an increase in circulating monocytes that peaked after 2 months of rIL-2 treatment, which then remained 2- to 3-fold elevated from baseline.

At the initiation of the study, the concentration of CD4+ T-cells in the HIV+ individuals was 338±26 cells/mm$^3$ (mean±SEM) as compared with 860±150 cells/mm$^2$ for normal individuals.

A progressive decline in CD4+ T-cells to 275±52 cells/mm$^3$ was observed after six months of therapy at the ≦125,000 IU rIL-2/m$^2$/day dose (Group 1). Mean monthly changes in CD4+ T-cells were calculated from the linear trends obtained from the mean of the slopes. A mean monthly gain in CD4+ T-cells of 26 cells/mm$^3$ was calculated for the groups receiving the intermediate and higher doses (Groups 3 and 4). A mean monthly loss of 28 CD4+ T-cells/mm$^3$, on the other hand, occurred in the group that received ≦125,000 IU rIL-2/m$^2$/day (Group 1) (p=0.01).

Example 10

Determination of Plasma HIV Conc. in Individuals in IL-2 Trial

Plasma HIV concentrations were determined at the beginning of the clinical trial of Examples 2 and 3 by branched chain DNA assays as described by Pachl et al. (Pachl et al., J. Acq. Immune Defic. Syndromes and Human Retrovirol. 8:446–54 (1995)). Thereafter, they were sent for assaying to Chiron, Corporation, Emeryville, Calif.

Example 11

Effect of IL-2 Therapy on Plasma HIV Conc. in Individuals in First Clinical Trial The first 6 individuals entered in the study were monitored for plasma HIV RNA levels with a branched chain DNA assay (bDNA) that had a sensitivity of 10,000 viral RNA molecules/ml. Only 2 of these individuals had detectable plasma HIV levels (14 and 20×10$^3$ viral RNA molecules/ml, respectively). The assays of these 2 individuals became negative after initiation of IL-2 treatment and remained so throughout the 6 months of the study.

The plasma HIV levels of the other 4 individuals remained negative during the 6 month study interval.

Subsequent to enrollment of the first 6 individuals, a second generation bDNA assay became available that is significantly more sensitive, and has a lower limit of detection of 500 HIV RNA molecules/ml. Accordingly, the next 8 individuals enrolled were monitored using the improved bDNA assay. At the initiation of IL-2 therapy, the mean plasma HIV concentration of these 8 individuals was 4428±2543 (SEM) RNA molecules/ml. Over the course of 6 months of IL-2 therapy, the mean HIV concentration fluctuated less than 2-fold, and at the end of the study the mean HIV concentration was not significantly different from that at the initiation of IL-2 treatment (5150±1984 (SEM) RNA molecules/ml).

Example 12

Preparation of IFN-γ for Administration

Recombinant human IFN-γ is obtained from Genentech (South San Francisco, Calif.). All dosages for the study are calculated in nmole IFN-γ.

Example 13

Profile of Patients Selected for IFN-γ Clinical Trial

Individuals over the age of 18 are eligible for enrollment in the trial if they test positive for HIV-reactive antibodies, if they are HIV p24 antigen negative, and if they have no concurrent opportunistic infections. In addition, the criteria for eligibility includes an absolute CD4+ T-cell count of between 200 and 500 cell/mm$^3$ and being placed on nucleoside-analogue antiretroviral medication (AZT, and 3TC).

Any individual that has any chronic illness unable to be controlled by medication, pregnant or nursing, or has any history of malignancy is excluded. Hematologic and biochemical criteria utilized for excluding individuals includes: total bilirubin >5 times normal, AST >90 IU, creatinine >2.0 mg/dl, neutrophils <100/mm$^3$, hemoglobin <10 mg/dl, platelets <75,000/mm$^3$.

35 individuals are enrolled. Before initiation of IFN-γ therapy, the CD4+ T-cell count is over 300. The group is homogeneous with respect to leukocyte and differential counts, and there were no differences in these parameters among the subjects are given different IFN-γ doses.

Example 14

Initiation of 1-year IFN-γ Clinical Trial

On the first day of therapy, all individuals participating in the study are admitted to the hospital. Each individual is given the initial subcutaneous injection of IFN-γ and, then, frequent blood samples are taken for the first 24 hours for IFN-γ to conduct pharmacokinetic studies. All subjects then receive instructions on the self-administration of IFN-γ by subcutaneous injection, and are seen subsequently on an out-patient basis weekly for 6 weeks, and then biweekly for a one (1) month study period.

Example 15

Doses and Regimes for Five IFN-γ Dose Groups

Group 1: 5 nmole IFN-γ/m$^2$/day 4 individuals self-administer 5 nmole IFN-γ/m$^2$/day for a period of 1 year. When any toxicity is observed which may be correlated with each IFN-γ inoculation is observed, the administration of IFN-γ is stopped. A confirmation is obtained when a cessation of IFN-γ administration results in the attenuation of symptoms.

Subsequently, the IFN-γ dose is reduced by 50%. When toxicity is encountered, the previous procedure is repeated and the dose lowered again, until a dose free of toxicity is found. for the afflicted individuals.

The individuals receiving 5 nmole IFN-γ/m$^2$/day who are unaffected by toxicity complete the course (1 year) of therapy.

Group 2: 2.5 nmole IFN-γ/m$^2$/day 4 individuals self-administer 2.5 nmole IFN-γ/m$^2$/day for 1 year. Any individuals having side effects at this or other doses is treated as described for Group 1 above to avoid toxicity, and to permit completion of the study without untoward effects.

Group 3: 10 nmole IFN-γ/m$^2$/day 4 individuals self-administration of 10 nmole IFN-γ/m$^2$/day, and complete the 1 year of therapy without any significant systemic symptoms.

Group 4: 7.5 nmole IFN-γ/m$^2$/day

A dose of 7.5 nmole IFN-γ/m$^2$/day is self-administered by 4 individuals for a full period of 1 year.

Group 5: 50 nmole IFN-γ/m$^2$/day 4 subjects receive 50 nmole IFN-γ/m$^2$/day. When individuals treated at this dose develop systemic symptoms after injections, and are unable to undergo further treatment at this dose level, the treatment is discontinued. Otherwise a full 1 year course is self-administered daily.

Example 16

Determination of Toxicity During IFN-γ Trial

Toxicity is defined as described in Example 5 above. If, and when, DLT occurs in any one individual, treatment is withheld from that particular individual until the toxic symptoms or signs are resolved. Treatment is then resumed at an IFN-γ dose midway between the previous dose level and the current dose (the dose is halved). The objective is to achieve a dose that is non-toxic but that would permit each subject to carry out normal daily activities.

Example 17

Determination of IFN-γ Plasma Concentration

Plasma IFN-γ concentrations are determined by ELISA (Endogen, Inc., Boston, Mass.), according to the manufacturer's specification. The lower limit of detection of IFN-γ in plasma is 0.5 pM.

Example 18

Pharmacokinetic Studies for IFN-γ Trial

The IFN-γ plasma concentration is determined at frequent intervals over the first 24 hours after each dose increment is administered. A marked increase in the detectable IFN-γ plasma level is observed when following the time course at higher doses when compared with the profile obtained at lower doses.

The concentrations of IFN-γ that saturate about 50% of the high affinity receptors (about 100 pM) are detectable even hours after the injection. Thereafter, the measurement of trough IFN-γ plasma levels just prior to the next dose further daily doses of IL-2 does not result in gradual increases plasma IFN-γ levels.

Example 19

Determination of Circulating Leukocyte Count for Individuals in IFN-γ Clinical Trial The determinations of leukocyte types and concentrations are performed by tricolor flow cytometry using monoclonal antibodies directly conjugated with fluorochromes as described by Stewart and Stewart (Stewart, C. and Stewart, S., "Cell Preparation for the Identification of Leukocytes", Darynkiewicz Z., Robinson, J., Crissman H., Eds., in Methods in Cell Biology, pp. 39–60 (1994)).

Example 20

Effect of IFN-γ Therapy on Leukocyte Production by Individuals in Clinical Trial The data on leukocyte production obtained from the different groups is analyzed separately and compared with one another over the 1 year period of treatment.

Example 21

Determination of Plasma HIV Concentration

Plasma HIV concentrations are determined at the beginning of the clinical trial of Examples 2 and 3 by branched chain DNA assays as described by Pachl et al. (Pachl et al., J. Acq. Immune Defic. Syndromes and Human Retrovirol. 8:446–54 (1995)). Thereafter, they are sent for assaying to Chiron, Corporation, Emeryville, Calif.

Example 22

Comparison of Joint Antiviral/IFN-γ Therapy with Treatment with Antiviral Alone of Asymptomatic HIV+ Individuals This comparison between the results obtained in the randomized AZT plus low doses of IFN-γ immunotherapy clinical trial described in Examples 12 and 13, and a similar study (the Concord study) conducted solely with AZT, demontrates that the combined long term therapy affords an unexpected synergy over the AZT alone treatment.

The Concorde study is a double blind randomized study on the administration of AZT to asymptomatic HIV+ individuals (The Lancet 343: 871–881 (1994)). The recruited individuals were divided into two groups, an early administration group and a second group where AZT administration was started after the individual's T-cell count fell below a certain figure or the individual developed ARC or AIDS. AZT was administered at a dose of 250 mg four times per day to 877 asymptomatic HIV+ individuals and a control group of 872 individuals were given a placebo. The individuals were followed-up until death or for 3 years. Of the placebo group, 418 started AZT treatment at some point in the trial, 174 after developing ARC or AIDS, and the remainder based on their low CD4+ cell counts. No statistical difference was observed between the two regimes in the results observed.

As described in Examples 12 and 13 above, the combination of anti-viral treatment with immunotherapy with the present low doses of IFN-γ provides unexpected benefits when compared with anti-viral therapy alone. While artisans with skill in the art have been utilizing substantially higher doses of IFN-γ for therapy, the present low dose regime in combination with an anti-viral drug produces anti-viral effects with a concomitant stimulation of the immune system, in the absence of toxicity WHO Grade 1 or higher. Thus, the combined therapy precludes the onset of immunodeficiency and the clinical diagnosis of ARC and AIDS without the toxicity observed with other treatments.

Moreover, in the Concord study, after the first 6 months of therapy the concentration of circulating CD4+ T-cells was unchanged from base line in both, the AZT-treated and in the placebo-treated, groups. On the basis of the clinical trial of Examples 12 and 13 above, the present immunotherapy produces increase concentration of circulating CD4+ T-cells.

Example 23

IFN-γ Immunotherapy of Normal Individuals

This experiment demonstrates the beneficial effect of IL-12 when self-administered in low doses by normal individuals for fighting infections, such as the common cold, the grippe, and the flu.

Group 1: IFN-γ Immunotherapy 10 normal individuals are recruited into the study and given individually sealed 10 nmole IFN-γ/m$^2$/daily doses for self administration, when signs of a cold, fever, myalgia, cough, or rhinitis appear. The individuals self-administer the IFN-γ before and during the course of the infection and resolution of the symptoms of the cold or flu.

Group 2: Placebo 10 normal individuals are recruited and given sealed daily dose of placebo for self-administration as in group 1.

All individuals in this study report on the development of their infections, symptoms, including dates, and severity, on a scale of 1 to 10, from the mildest to most severe symptoms, including temperature, ambulatory ability, body aches, nasal mucosity, fatigue, cough, nausea, and vomiting. Results are recorded twice daily until the resolution of all symptoms. Individuals are monitored 3 times per week as ambulatory patients by a trained investigator.

The individuals in Group 1 greatly benefit from the treatment in comparison with Group 2, particularly with regard to the rate of onset of symptoms, and the rate of resolution of symptoms.

Example 24

Confirmation of Potentiation of Combined IFN-γ/Anti-viral Therapy vs. Antiviral Therapy Alone This experiment confirms a synergistic effect of antiviral therapy plus IFN-γ immunotherapy, as shown by improved immune function. When administered to HIV+ asymptomatic individuals, antiviral therapy alone decreases CD4+ T-cell destruction. On the other hand, IL-12 immunotherapy is shown to stimulate CD4+ T-cell production.

50 asymptomatic HIV+ individuals are recruited early in the course of HIV infection, with CD4+ T-cell counts >500 cells/mm$^3$ of blood. The individuals are randomized to receive antiviral therapy vs. antiviral therapy plus IFN-γ immunotherapy. 25 individuals are placed in each treatment group.

Group 1: Anti-viral Therapy Alone

Antiviral therapy consists of a combination of the nucleoside analogues zidovudine (AZT, 600 mg/day), lamivudine (3TC, 300 mg/day), and the protein inhibitor invirase (600 mg/day).

Group 2: Combined Anti-viral/IFN-γ Therapy 25 individuals receive anti-viral therapy as in Group 1 plus IFN-γ over the same period of time. The IFN-γ is self-administered daily by subcutaneous injection at 10 nmole IFN-γ/m$^2$/day.

All individuals are monitored as detailed above, for clinical signs and symptoms of toxicity, and laboratory tests for functional abnormalities of the major organ systems are done. Plasma HIV levels are determined by the bDNA assay of Pachl et al. (1995), supra, and immunological tests conducted include cutaneous tests for delayed-type hypersensitivity (DTH), and white blood cell (WBC) enumeration by flow cytometry.

For statistical analysis, linear trends in cell counts and HIV plasma levels over time are calculated by computing linear regression slopes separately for each subject, and then the average slopes for each treatment group is compared using the Students' T test. Following 6 months of therapy, each treatment group is crossed-over to the alternative therapy, and the study continues for an additional 6 months.

Example 25

Clinical Trial with IFN-γ Immunotherapy on Individuals with Congenital and Acquired Immunodeficiencies 10 individuals suffering from congenital immunodeficiencies, particularly those due to an inability to produce IFN-γ, and individuals suffering from acquired immunodeficiencies that are not secondary to HIV infection, such as common variable immunodeficiencies, and immunodeficiencies following cytotoxic treatments for cancer (e. g., chemotherapy and radiotherapy), are recruited for IL-12 immunotherapy providing chronic immune stimulation with IFN-γ. These individuals self-administer IFN-γ treatment protocols for 6 months to 1 year, similar to those employed for asymptomatic HIV+ individuals, shown in Example 3 above, except that they do not receive AZT. The daily dose self-injected is 10 nmole IFN-γ/m$^2$ body surface. Noticeable improvement is noticed with respect to the initial symptomatology, including suceptibility to infections, particularly those caused by opportunistic organisms, and by a reduced requirement for other immune enhancing therapies, such as the administration of i.v. immunoglobulin.

Example 26

Clinical Trial with IFN-γ Immunotherapy for Individuals Suffering from Microbial Infections This experiment has been set up to demonstrate that microbial infections, especially chronic infections, benefit from low dose, chronic IFN-γ immune stimulation. Examples of microbial infections are, for example, those due to viruses (e. g., hepatitis viruses), mycobacteria (e. g., tuberculosis, especially multi-drug-resistant M. tuberculosis), fungi (e. g., candidiasis, aspergillosis, histoplasmosis, coccidiomycosis, and nocardiosis), and parasites (e. g., toxoplasmosis, pneumocystosis), benefit from chronic immune stimulation.

10 individuals are recruited into this study, which are afflicted by a microbial infection, and evidencing low immune system activity. Each individual self-administers 10 nmole IFN-γ/m$^2$/day over a period of up to 6 months to 1 year and, depending on the severity and criticality of symptoms, periodic tests are conducted as described in Example 16 above. Amelioration of overall symptoms associated with increased immune response is observed.

Example 27

Clinical Trial with IFN-γ Immunotherapy for Cancer Patients without Residual Detectable Malignancy after Primary Anti-cancer Therapy This experiment is conducted to demonstrate that chronic IFN-γ immunotherapy is beneficial for individuals afflicted with various cancers, such as malignant melanoma, renal cell carcinoma, breast carcinoma, non-Hodgkins lymphoma, Hodgkins lymphoma, leukemia, and multiple myeloma. A daily maintenance dose of 10 nmole IFN-γ/m$^2$ is self-administered by each individual, and tests are conducted as described above in Examples 15 and 16.

10 individuals are recruited into this study, all of whom have received a course of anti-cancer therapy, and have been determined not to have any malignant cells or tissue by standard tests, such as x-ray, CT scans or blood tests. The individuals are divided randomly into two groups.

Group 1: Placebo 5 individuals self-administer placebo without IFN-γ or other medication.

Group 2: IFN-γ Immunotherapy

Five individuals self-administer 10 nmole IFN-γ/m$^2$ per day. The overall beneficial effect is determined by the duration of the interval the individual remains tumor-free and by the individual's survival.

Example 28

IFN-γ Therapy Administered by other Routes

This experiment has been designed to demonstrate that chronic IFN-γ immunotherapy, in accordance with this invention, is beneficial without eliciting substantial toxicity WHO Grade 1 or higher, when administered by routes other than injection.

Ten individuals are recruited into the study, including normal individuals, individuals afflicted with cancer, and invididuals infected with HIV and other microbial infections, and congenital and acquired immunodeficiencies. All individuals are matched with at least one corresponding individual, who self-administered IL-12 by injection under similar conditions.

All individuals are instructed as described in Example 3 above to self-apply a patch or to inhale a daily dose of 10 nmole/m$^2$ of IFN-γ for 6 months to 1 year. All individuals in this study report on their progress, including symptoms, severity, and others, and date of occurrence, scoring on a scale of 1 to 10, from the mildest to the most severe symptoms, including fever, fatigue, myalgia, nausea, and vomiting. The results obtained are similar to those when IFN-γ immunotherapy is conducted by injection.

Example 29

Therapy Utilizing Different Forms of the Agents

This experiment is conducted to show that immunotherapy with analogs of IFN-γ afford to the individuals results similar to immunotherapy with IFN-γ itself, in terms of benefits observed in the substantial absence of toxicity WHO grade 1 or higher.

Ten individuals are recruited into this study, including normal individuals, individuals afflicted with cancer, HIV and other microbial infections, and congenital and acquired immunodeficiencies.

A dose of derivatized IFN-γ corresponding to 10 nmole/m$^2$ of IFN-γ is self-administered daily by subcutaneous injection by each individual over a period of 6 months to 1 year. A dose of mutated IFN-γ corresponding to 10 nmole/m$^2$ IFN-γ is self-administered daily by each individual for a period of six months. A dose of mutated X-IFN-γ corresponding to 10 nmole/m$^2$ of IFN-γ is self administered daily by each individual for a period of six months. Tests and reports are as described above. Each individual is matched with an individual receiving recombinant IFN-γ by injection as described in Example 3 above. Results, beneficial to the individuals when compared to controls, which are similar to those obtained with recombinant IL-12 immunotherapy are observed.

Example 30

Clinical Trial of IL-15

The set-up of this trial is similar to the one described in Examples 1 to 4 for IL-2. The trial is conducted for at least 6 months and results in therapeutically beneficial results.

Example 31

Clinical Trial of the CD40 Ligand

This cytokine is tried as adjuvant therapy for hepitits B and C vaccines, since it is active in B-cell activation and proliferation. Therapeutically beneficial effects are seen.

Example 32

Clinical Trial of Natural IFN-2

IFN-α is self-administered by individuals as described in Example 4 above, produces therapeutically beneficial results.

Example 33

Clinical Trial of IFN-B

This trial is also conducted as taught by the present invention. The IFN-β agent within the dosage prescribed is self-administered by individuals with therapeutically beneficial results.

Having now generally described the invention, as well as by reference to the examples, an artisan will understand that many variations may be applied that are within the confines of the invention.

What is claimed as novel and unobvious in Letters Patent of the United States is:

1. A method of administering or applying to, or self-applying by, a subject a composition comprising an agent selected from natural and recombinant IL-2 and mixtures thereof, for a period greater than three months under conditions effective to release an amount effective to activate high affinity interleukin and/or interferon receptors and enhance immune function in the absence of the symptoms of toxicity Grade 1 or higher, as depicted in FIG. 1A and FIG. 1B.

2. The method of claim 1, wherein the composition further comprises a physiologically acceptable carrier.

3. The method of claim 2, wherein the carrier comprises a pharmaceutically or veterinarily acceptable carrier.

4. The method of claim 1, wherein the composition is administered, applied, self-administered, or self-applied subcutaneously, intramuscularly, intradermally, intralymphatically, intra tumor, transdermally, intracavitarily, transbuccally, transpulmonarily, transmucosally, orally, intra nasally, intra vaginally, intra anally, intra buccally, sublingually, by inhalation, or by implant.

5. The method of claim 1, further comprising adjusting the agent's dose by monitoring the blood concentration of the agent, the % saturation of the high affinity cytokine receptors, or the blood count of at least a cell type selected from the group consisting of circulating lymphocytes, monocytes and polymorphonuclear leukocytes.

6. The method of claim 1, wherein the composition is self-administered.

7. The method of claim 1, wherein the composition is administered, applied, self-administered, or self-applied in the form of a powder, a tablet, a capsule, a dragee, a cream, a solution, a suspension, an emulsion, a gel, a spray, a controlled release formulation, liposome or other micelles, or combinations or mixtures thereof and, if needed, is formulated prior to administration, application, self-administration, or self-application.

8. The method of claim 7, wherein the composition is a controlled release formulation.

9. The method of claim 7, wherein the composition is an inhalable formulation, and is administered, applied, self-administered, or self-applied by means of an inhaler.

10. The method of claim 7, wherein the composition is a topical formulation, further comprising a carrier or diluent for the agent suitable for topical delivery, and optionally an ingredient selected from the group consisting of buffers, salt forming acids and bases, perfumes, colorants, emollients, adjuvants, single or multiple enteric coatings, copolymers, microporous or semi-permeable membranes, enzyme inhibitors, mucoadhesives, chelating agents, particulate systems, viral envelope proteins, liposomes and other micelles, emulsifiers, lipoproteins and other fatty acid derivatives, surfactants, bile salts, hydrophilic, neutral, and hydrophobic polymers and co-polymers, hydrogels, biodegradable polymers and co-polymers, and an additional bioactive agent consisting of anti-viral agents in an amount and under conditions effective to facilitate the passage onto and through the subject's dermal, mucosal or pulmonary surface of a daily dose of the agent.

11. The method of claim 10, wherein the topical formulation is a cream, an ointment, a solution, a gel, a powder, a suspension, an emulsion, encapsulated particles or mixtures thereof.

12. The method of claim 11, wherein a solution or suspension of the composition is comprised in, and delivered from, a compartment of a transdermal device.

13. The method of claim 12, wherein the device is an electrotransport or ultrasound device.

14. The method of claim 7, wherein the composition is formulated as a vaccine.

15. The method of claim 1, wherein the composition is in solid form, and is formulated prior to administration, application, self-administration, or self-application.

16. The method of claim 15, wherein the composition is in lyophilized form.

17. The method of claim 1, wherein the composition is in liquid form.

18. The method of claim 1, wherein the composition is administered, applied, self-administered, or self-applied as a therapeutic product comprising the agent, which when administered or applied to, or self-administered or self-applied by, the subject releases the desired amount of the agent over a pre-determined period of time effective to activate, and maintain activated for the period of time, high affinity agent receptors without producing substantial toxicity of grade 1 or higher, as depicted in FIG. 1A and FIG. 1B.

19. The method of claim 18, wherein the product is in the form of a patch, an implant or a suppository.

20. The method of claim 1, wherein the composition further comprises an ingredient selected from the group consisting of carriers, diluents, buffers, salt forming acids and bases, perfumes, colorants, emollients, adjuvants, single or multiple enteric coatings, copolymers, midroporous or semi-permeable membranes, enzyme inhibitors, mucoadhesives, chelating agents, particulate systems, viral envelope proteins, liposomes and other micelles, emulsifiers, lipoprotein and other fatty acid derivatives, surfactants, bile salts, hydrophilic, neutral, and hydrophobic polymers and co-polymers, hydrogens, biodegradable polymers and co-polymers, and anti-inflammatories, an additional bioactive agent consisting of anti-viral agents.

21. The method of claim 1, wherein the composition is parenteral formulation.

22. The method of claim 21, wherein the parenteral formulation is an injectable formulation.

23. The method of claim 22, wherein the injectable formulation is administered, applied, self-administered, or self-applied subcutaneously, intravenously, or intraperitoneally.

24. The method of claim 1, wherein the agent is present in an amount of about 0.0001 to 50 wt % of the composition.

25. The method of claim 1, wherein the subject is a normal subject or a subject afflicted with a condition associated with a viral microorganism.

26. The method of claim 25, wherein the subject is HIV seropositive, and the composition is administered in an amount and under conditions which substantially avoid increasing the count of circulating microorganism.

27. The method of claim 1, wherein the subject is an animal.

28. The method of claim 27, wherein the animal is a human.

29. The method of claim 1, wherein the amount of the agent administered is effective to elevate the blood count of at least one blood cell type selected from the group consisting of circulating lymphocytes, monocytes and polymorphonuclear leukocytes.

30. The method of claim 29, wherein the amount of the agent administered is effective to elevate the blood count of at least one blood cell selected from the group consisting of circulating T-cells, B-cells, NK cells, monocytes, eosinophils, neutrophils, basophils and antigen-presenting cells.

31. The method of claim 1, wherein the composition is administered as an implant.

32. The method of claim 1, further comprising administering or applying to, self-administering or self-applying by, the subject one or more ant-viral agents.

33. The method of claim 32, wherein the anti-viral agents are selected from the group consisting of nucleotide analogues and protease inhibitors.

34. The method of claim 33, wherein the subject is a normal subject or a subject afflicted with a condition associated with a viral microorganism.

35. The method of claim 34, wherein the subject is HIV seropositive, and the composition is administered in an amount and under conditions which substantially avoid increasing the count of circulating microorganism.

36. The method of claim 34, wherein the subject is hepatitis-C seropositive, and the composition is administered in an amount and under conditions which substantially avoid increasing the count of circulating microorganism.

37. The method of claim 32, wherein the subject is administered, applied, self-administers or self-applies, one or more anti-viral agents selected from the group consisting of zidovudine (AZT), 2',3'-dideoxyinosine (ddl), 3'-azido-2',3'-dideoxythymidine, d4T, acyclovir, 1,3-dihydro-2-propoxy-methyquanine (gancyclovir), ribavirin, dideoxycytidine (ddC), lamivudine (3TC), and enzyme inhibitors.

38. The method of claim 37, wherein the subject is administered or applied, self-administers or self-applies one or more enzyme inhibitors, and the enzyme inhibitors comprise protease inhibitors.

39. The method of claim 38, wherein the protease inhibitors are saquinovir or invirase.

40. The method of claim 39, wherein the subject is administered or applied, self-administers or self-applies one or more anti-viral agents, and the anti-viral agents are selected from the group consisting of zidovudine (AZT), lamivudine (3TC), d4T, invirase and combinations thereof.

41. The method of claim 40, wherein the anti-viral agent combinations administered, applied, self-administered or self-applied comprise zidovudine (AZT), lamivudine (3TC), and d4T, or
zidovudine (AZT), lamivudine (3TC), and invirase.

42. The method of claim 41, wherein the anti-viral agent combination administered, applied, self-administered or self-applied comprises zidovudine (AZT), lamivudine (3TC), and invirase, and zidovudine is administered, applied, self-administered or self-applied at about 600 mg/day, lamivudine (3TC) at about 300 mg/day, and invirase at about 600 mg/day.

43. A method of administering or applying to, or self-administering or self-applying by, a subject a composition comprising an agent selected from natural and recombinant IL-2 and mixtures thereof, for a period greater than three months under conditions effective to release an amount effective to activate high affinity IL-2 receptors and enhance immune function in the absence of the symptoms of toxicity Grade 1 or higher, as depicted in FIG. 1A abd FIG 1B.

44. The method of claim 43, wherein the composition further comprises a physiologically acceptable carrier.

45. The method of claim 43, wherein the composition is administered, applied, self-administered, or self-applied subcutaneously, intramuscularly, intradermally, intralymphatically, intratumor, transdermally, intracavitarily, transbuccally, transpulmonarily, transmucosally, orally, intranasally, intravaginally, intraanally, intrabuccally, sublingually, by inhalation, or by implant.

46. The method of claim 43, further comprising adjusting the agent's dose by monitoring the blood concentration of the agent, the % saturation of the high affinity IL-2 receptors, or the blood count of at least a cell type selected from the group consisting of circulating lymphocytes, monocytes and polymorphonuclear leukocytes.

47. The method of claim 43, wherein the composition is administered, applied, self-administered, or self-applied as a therapeutic product comprising the agent, which when administered or applied to, or self-administered or self-applied by, the subject releases the desired amount of the agent over a pre-determined period of time effective to activate, and maintain activated for the period of time, high affinity agent receptors without producing substantial toxicity symptoms of grade 1 or higher as depicted in FIG. 1A and 1B.

48. The method of claim 43, wherein the composition further comprises an ingredient selected from the group consisting of carriers, diluents, buffers, salt forming acids and bases, perfumes, colorants, emollients, adjuvants, single or multiple enteric coatings, copolymers, microporous or semi-permeable membranes, enzyme inhibitors, mucoadhesives, chelating agents, particulate systems, viral envelope proteins, liposomes and other micelles, emulsifiers, lipoproteins and other fatty acid derivatives, surfactants, bile salts, hydrophilic, neutral, and hydrophobic polymers and co-polymers, hydrogels, biodegradable polymers and co-polymers, and anti-inflammatories, an additional bioactive agent consisting of anti-viral agents.

49. The method of claim 43, wherein the agent is present in an amount of about 0.0001 to 50 wt % of the composition.

50. The method of claim 43, wherein the subject is a normal subject or a subject afflicted with a condition associated with a viral microorganism.

51. The method of claim 43, wherein the subject is HIV seropositive, and the composition is administered in an amount and under conditions which substantially avoid increasing the count of circulating microorganism.

52. The method of claim 43, wherein the subject is a human.

53. The method of claim 43, wherein the amount of the agent administered is effective to elevate the blood count of at least one blood cell type selected from the group consisting of circulating lymphocytes, monocytes and polymorphonuclear leukocytes.

54. The method of claim 43, wherein the amount of the agent administered is effective to elevate the blood count of at least one blood cell selected from the group consisting of circulating T-cells, B-cells, NK cells, monocytes, eosinophils, neutrophils, basophils and antigen-presenting cells.

55. The method of claim 43, further comprising administering or applying to, self-administering or self-applying by, the subject a bioactive agent consisting of anti-viral agents.

56. The method of claim 43, wherein the subject is administered or applied, or self-administers, or self-applies, the agent and one or more bioactive agents consisting of anti-viral agents.

57. A method of increasing and/or maintaining the count of circulating blood cells selected from the group consisting of lymphocytes, monocytes, and polymorphonuclear leukocytes, comprising conducting the method of claim 43, wherein the composition is administered, applied, self-administered, or self-applied for a period greater than three months under conditions effective to release an amount effective to increase and/or maintain circulating blood cell count.

* * * * *